US007118751B1

(12) United States Patent
Ledbetter et al.

(10) Patent No.: US 7,118,751 B1
(45) Date of Patent: Oct. 10, 2006

(54) DNA VACCINES ENCODING ANTIGEN LINKED TO A DOMAIN THAT BINDS CD40

(75) Inventors: Jeffrey A Ledbetter, Shoreline, WA (US); Martha Hayden-Ledbetter, Shoreline, WA (US)

(73) Assignee: Trubion Pharmaceuticals, Inc., Seattle, WA (US)

( * ) Notice: Subject to any disclaimer, the term of this patent is extended or adjusted under 35 U.S.C. 154(b) by 708 days.

(21) Appl. No.: 09/687,864

(22) Filed: Oct. 13, 2000

Related U.S. Application Data

(60) Provisional application No. 60/159,690, filed on Oct. 14, 1999.

(51) Int. Cl.
*A61K 39/00* (2006.01)
(52) U.S. Cl. ............... 424/192.1; 424/188.1; 424/208.1; 424/153.1; 424/143.1; 424/178.1; 530/350
(58) Field of Classification Search ............. 424/188.1, 424/208.1, 192.1, 153.1, 143.1, 178.1; 530/350
See application file for complete search history.

(56) References Cited

U.S. PATENT DOCUMENTS

| | | | |
|---|---|---|---|
| 5,521,288 A | 5/1996 | Linsley et al. |
| 5,540,926 A | 7/1996 | Aruffo et al. |
| 5,580,773 A | 12/1996 | Kang et al. |
| 5,658,762 A | 8/1997 | Zanetti et al. |
| 5,698,679 A | 12/1997 | Nemazee et al. |
| 5,945,513 A | 8/1999 | Aruffo et al. |
| 5,962,406 A | 10/1999 | Armitage et al. |
| 5,981,724 A | 11/1999 | Armitage et al. |
| 6,086,875 A | 7/2000 | Blumberg et al. |
| 6,113,901 A | 9/2000 | Bluestone et al. |

OTHER PUBLICATIONS

Howell, A.L., et al., "Targeting HIV-1 to FcgammaR on human phagocytes via bispecific antibodies reduces infectivity of HIV-1 to T cells." J. of Leuk. Biol. 55: 385-391 (1994).
Zaghouani, H., et al., "Induction of antibodies to the human immunodeficiency virus type I by immunization of baboons with immunoglobulin molecules carrying the principal neutralizing determinant of the envelope protein." PNAS 92: 631-635 (1995).
Syrengelas, A.D., et al., "DNA Immunization induces protective immunity against B-cell lymphoma." Nature Med. 2: 1038-1041 (1996).

(Continued)

*Primary Examiner*—Jeffrey S. Parkin
(74) *Attorney, Agent, or Firm*—Marshall, Gerstein & Borun LLP

(57) ABSTRACT

Vaccines that target one or more antigens to a cell surface receptor improve the antigen-specific humoral and cellular immune response. Antigen(s) linked to a domain that binds to a cell surface receptor are internalized, carrying antigen(s) into an intracellular compartment where the antigen(s) are digested into peptides and loaded onto MHC molecules. T cells specific for the peptide antigens are activated, leading to an enhanced immune response. The vaccine may comprise antigen(s) linked to a domain that binds at least one receptor or a DNA plasmid encoding antigen(s) linked to a domain that binds at least one receptor. A preferred embodiment of the invention targets HIV-1 env antigen to the CD40 receptor, resulting in delivery of antigen to CD40 positive cells, and selective activation of the CD40 receptor on cells presenting HIV-1 env antigens to T cells.

14 Claims, 7 Drawing Sheets

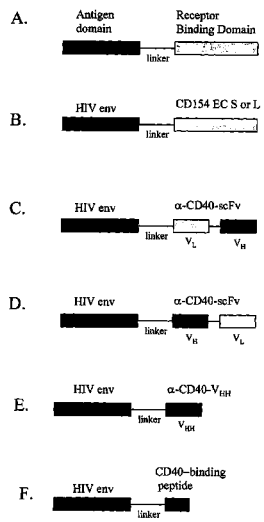

Fusion Proteins that Target Antigen to APC

OTHER PUBLICATIONS

Liu, C., et al., "Fcgamma RIII on Human B Cells Can Mediate Enhanced Antigen Presentation." Cell. Immunol. 167: 188-194. (1996).

Liu, C., et al., "FcgammaRI-Targeted Fusion Proteins Result in Efficient Presentation by Human Monocytes of Antigenic and Antagonist T Cell Epitopes." J. Clin. Invest. 98: 2001-2007. (1996).

Guyre, P.M., et al., "Increased Potency of Fc-receptor-targeted antigens." Cancer Immunol. Immunother. 45: 146-148 (1997).

Boyle, J.S., et al., "Enhanced responses to a DNA vaccine encoding a fusion antigen that is directed to sites of immune induction." Nature 392: 408-411 (1998).

Guyre, P.M., et al., "Macrophage-targeted killing and vaccines." Res. Immunol. 149: 655-660 (1998).

Serre, K., et al., "Efficient Presentation of Multivalentantigens Targeted to Various Cell Surface Molecules of Dendritic Cells and Surface Is of Antigen Specific B Cells." J. Immunol. 161: 6059-6067. (1998).

Rodriguez, D., et al., "A human immunodeficiency virus type 1 Env-granulocyte macrophage colony-stimulating factor fusion protein enhances the cellular immune response to Env in a vaccinia virus-based vaccine." J. of Gen Virol. 80: 217-223. (1999).

Biragyn, A., et al., "Genetic fusion of chemokines to a self tumor antigen induces protective, T-cell dependent antitumor immunity." Nature Biotech. 17: 253-258. (1999).

Figure 1.
Fusion Proteins that Target Antigen to APC

A. Antigen domain — linker — Receptor Binding Domain

B. HIV env — linker — CD154 EC S or L

C. HIV env — linker — α-CD40-scFv ($V_L$, $V_H$)

D. HIV env — linker — α-CD40-scFv ($V_H$, $V_L$)

E. HIV env — linker — α-CD40-$V_{HH}$ ($V_{HH}$)

F. HIV env — linker — CD40-binding peptide

Figure 2A.
Sequence and translation of two cDNAs encoding HIV gp120 V3 loop-CD154
LONG form extracellular domain fusion proteins.

```
     HindIII
     ~~~~~~~~        Signal Peptide
                     Met Leu Tyr Thr Ser Gln Leu Leu Gly Leu Leu
  1  AAG CTT GCC GCC ATG CTG TAT ACC TCT CAG CTG TTA GGA CTA CTT
                                 BglII
                                 ~~~~~~~~ HIVgp120-V3 loop
     Leu Phe Trp Ile Ser Ala Ser Arg Ser Val Val Ile Asn Cys Thr
 46  CTG TTT TGG ATC TCG GCT TCG AGA TCT GTA GTA ATT AAT TGT ACA
     Arg Pro Asn Asn Asn Thr Arg Arg Arg Leu Ser Ile Gly Pro Gly
 91  AGA CCC AAC AAC AAT ACA AGA AGA AGG TTA TCT ATA GGA CCA GGG
     Arg Ala Phe Tyr Ala Arg Arg Asn Ile Ile Gly Asp Ile Arg Gln
136  AGA GCA TTT TAT GCA AGA AGA AAC ATA ATA GGA GAT ATA AGA CAA
     Ala His Cys Asn Ile Ser
181  GCA CAT TGT AAC ATT AGT
     ProAspPro Linker
        BamHI
        ~~~~~~~~
     Pro Asp Pro
199  CCG GAT CCA OR (Gly4Ser)3 Linker                                      BamHI
                                                               ~~~~~~~~
     Gly Gly Gly Gly Ser Gly Gly Gly Gly Ser Gly Gly Gly Gly Ser Asp Pro
199  GGT GGC GGT GGC TCA GGA GGC GGT GGA TCT GGC GGT GGA GGT TCG GAT CCA CD154 LONG extracellular domain
208PDP   Arg Arg Leu Asp Lys Ile Glu
250GS    AGA AGG TTG GAC AAG ATA GAA
229PDP   Asp Glu Arg Asn Leu His Glu Asp Phe Val Phe Met Lys Thr Ile
271GS    GAT GAA AGG AAT CTT CAT GAA GAT TTT GTA TTC ATG AAA ACG ATA
274PDP   Gln Arg Cys Asn Thr Gly Glu Arg Ser Leu Ser Leu Leu Asn Cys
316GS    CAG AGA TGC AAC ACA GGA GAA AGA TCC TTA TCC TTA CTG AAC TGT
319PDP   Glu Glu Ile Lys Ser Gln Phe Glu Gly Phe Val Lys Asp Ile Met
361GS    GAG GAG ATT AAA AGC CAG TTT GAA GGC TTT GTG AAG GAT ATA ATG
364PDP   Leu Asn Lys Glu Glu Thr Lys Lys Glu Asn Ser Phe Glu Met Gln
406GS    TTA AAC AAA GAG GAG ACG AAG AAA GAA AAC AGC TTT GAA ATG CAA
409PDP   Lys Gly Asp Gln Asn Pro Gln Ile Ala Ala His Val Ile Ser Glu
451GS    AAA GGT GAT CAG AAT CCT CAA ATT GCG GCA CAT GTC ATA AGT GAG
454PDP   Ala Ser Ser Lys Thr Thr Ser Val Leu Gln Trp Ala Glu Lys Gly
496GS    GCC AGC AGT AAA ACA ACA TCT GTG TTA CAG TGG GCT GAA AAA GGA
499PDP   Tyr Tyr Thr Met Ser Asn Asn Leu Val Thr Leu Glu Asn Gly Lys
541GS    TAC TAC ACC ATG AGC AAC AAC TTG GTA ACC CTG GAA AAT GGG AAA
544PDP   Gln Leu Thr Val Lys Arg Gln Gly Leu Tyr Tyr Ile Tyr Ala Gln
586GS    CAG CTG ACC GTT AAA AGA CAA GGA CTC TAT TAT ATC TAT GCC CAA
589PDP   Val Thr Phe Cys Ser Asn Arg Glu Ala Ser Ser Gln Ala Pro Phe
631GS    GTC ACC TTC TGT TCC AAT CGG GAA GCT TCG AGT CAA GCT CCA TTT
634PDP   Ile Ala Ser Leu Cys Leu Lys Ser Pro Gly Arg Phe Glu Arg Ile
676GS    ATA GCC AGC CTC TGC CTA AAG TCC CCC GGT AGA TTC GAG AGA ATC
679PDP   Leu Leu Arg Ala Ala Asn Thr His Ser Ser Ala Lys Pro Cys Gly
721GS    TTA CTC AGA GCT GCA AAT ACC CAC AGT TCC GCC AAA CCT TGC GGG
724PDP   Gln Gln Ser Ile His Leu Gly Gly Val Phe Glu Leu Gln Pro Gly
766GS    CAA CAA TCC ATT CAC TTG GGA GGA GTA TTT GAA TTG CAA CCA GGT
769PDP   Ala Ser Val Phe Val Asn Val Thr Asp Pro Ser Gln Val Ser His
811GS    GCT TCG GTG TTT GTC AAT GTG ACT GAT CCA AGC CAA GTG AGC CAT
814PDP   Gly Thr Gly Phe Thr Ser Phe Gly Leu Leu Lys Leu Glu *** ***
856GS    GGC ACT GGC TTC ACG TCC TTT GGC TTA CTC AAA CTC GAG TGA TAA
         XbaI
859PDP   ~~~~~~~
901GS    TCT AGA
```

Figure 2B.
Sequence and translation of two cDNAs encoding HIV gp120 V3 loop-
CD154 SHORT form extracellular domain fusion proteins.

```
        HindIII
        ~~~~~~~~        Signal Peptide
                        Met Leu Tyr Thr Ser Gln Leu Leu Gly Leu Leu
    1   AAG CTT GCC GCC ATG CTG TAT ACC TCT CAG CTG TTA GGA CTA CTT
                                    BglII HIVgp120-V3 loop
                                          ~~~~~~~~
        Leu Phe Trp Ile Ser Ala Ser Arg Ser Val Val Ile Asn Cys Thr
   46   CTG TTT TGG ATC TCG GCT TCG AGA TCT GTA GTA ATT AAT TGT ACA
        Arg Pro Asn Asn Asn Thr Arg Arg Arg Leu Ser Ile Gly Pro Gly
   91   AGA CCC AAC AAC AAT ACA AGA AGA AGG TTA TCT ATA GGA CCA GGG
        Arg Ala Phe Tyr Ala Arg Arg Asn Ile Ile Gly Asp Ile Arg Gln
  136   AGA GCA TTT TAT GCA AGA AGA AAC ATA ATA GGA GAT ATA AGA CAA
        Ala His Cys Asn Ile Ser
  181   GCA CAT TGT AAC ATT AGT ProAspPro Linker
                BamHI
                ~~~~~~~~
        ┌──────────────┐
        │Pro Asp Pro   │
  199   │CCG GAT CCA   │
        └──────────────┘

OR (Gly₄Ser)₃ Linker                                           BamHI
                                                                      ~~~~~~~~
        ┌─────────────────────────────────────────────────────────────────────────┐
        │ Gly Gly Gly Gly Ser Gly Gly Gly Gly Ser Gly Gly Gly Gly Ser Asp Pro     │
        │199GGT GGC GGT GGC TCA GGA GGC GGT GGA TCT GGC GGT GGA GGT TCG GAT CCA   │
        └─────────────────────────────────────────────────────────────────────────┘

CD154 SHORT extracellular domain
  208PDP       Glu Asn Ser Phe Glu Met Gln
  250GS        GAA AAC AGC TTT GAA ATG CAA
  229PDP       Lys Gly Asp Gln Asn Pro Gln Ile Ala Ala His Val Ile Ser Glu
  271GS        AAA GGT GAT CAG AAT CCT CAA ATT GCG GCA CAT GTC ATA AGT GAG
  274PDP       Ala Ser Ser Lys Thr Thr Ser Val Leu Gln Trp Ala Glu Lys Gly
  316GS        GCC AGC AGT AAA ACA ACA TCT GTG TTA CAG TGG GCT GAA AAA GGA
  319PDP       Tyr Tyr Thr Met Ser Asn Asn Leu Val Thr Leu Glu Asn Gly Lys
  361GS        TAC TAC ACC ATG AGC AAC AAC TTG GTA ACC CTG GAA AAT GGG AAA
  364PDP       Gln Leu Thr Val Lys Arg Gln Gly Leu Tyr Tyr Ile Tyr Ala Gln
  406GS        CAG CTG ACC GTT AAA AGA CAA GGA CTC TAT TAT ATC TAT GCC CAA
  409PDP       Val Thr Phe Cys Ser Asn Arg Glu Ala Ser Ser Gln Ala Pro Phe
  451GS        GTC ACC TTC TGT TCC AAT CGG GAA GCT TCG AGT CAA GCT CCA TTT
  454PDP       Ile Ala Ser Leu Cys Leu Lys Ser Pro Gly Arg Phe Glu Arg Ile
  496GS        ATA GCC AGC CTC TGC CTA AAG TCC CCC GGT AGA TTC GAG AGA ATC
  499PDP       Leu Leu Arg Ala Ala Asn Thr His Ser Ser Ala Lys Pro Cys Gly
  541GS        TTA CTC AGA GCT GCA AAT ACC CAC AGT TCC GCC AAA CCT TGC GGG
  544PDP       Gln Gln Ser Ile His Leu Gly Gly Val Phe Glu Leu Gln Pro Gly
  586GS        CAA CAA TCC ATT CAC TTG GGA GGA GTA TTT GAA TTG CAA CCA GGT
  589PDP       Ala Ser Val Phe Val Asn Val Thr Asp Pro Ser Gln Val Ser His
  631GS        GCT TCG GTG TTT GTC AAT GTG ACT GAT CCA AGC CAA GTG AGC CAT
  634GS        Gly Thr Gly Phe Thr Ser Phe Gly Leu Leu Lys Leu Glu * *
  676GS        GGC ACT GGC TTC ACG TCC TTT GGC TTA CTC AAA CTC GAG TGA TAA
                XbaI
                ~~~~~~~~
  679PDP       Ser Arg
  721GS        TCT AGA
```

Figure 3A.
Sequence and translation of two cDNAs encoding HIV gp120-CD154 LONG
form extracellular domain fusion proteins.

```
      HindIII
      ~~~~~~~~        Signal Peptide
                      Met Leu Tyr Thr Ser Gln Leu Leu Gly Leu Leu
  1   AAG CTT GCC GCC ATG CTG TAT ACC TCT CAG CTG TTA GGA CTA CTT
                              BglII
                              ~~~~~~~~    HIV gp120 domain
      Leu Phe Trp Ile Ser Ala Ser Arg Ser Met Leu Leu Gly Ile Leu
 46   CTG TTT TGG ATC TCG GCT TCG AGA TCT ATG CTC CTT GGG ATA TTG
      Met Ile Cys Ser Ala Thr Glu Lys Leu Trp Val Thr Val Tyr Tyr
 91   ATG ATC TGT AGT GCT ACA GAA AAA TTG TGG GTC ACA GTC TAT TAT
      Gly Val Pro Val Trp Arg Glu Ala Thr Thr Thr Leu Phe Cys Ala
136   GGG GTA CCT GTG TGG AGA GAA GCA ACC ACC ACT CTA TTT TGT GCA
      Ser Asp Ala Lys Ala Tyr Asp Thr Glu Val His Asn Val Trp Ala
181   TCA GAT GCT AAA GCC TAT GAT ACA GAG GTA CAT AAT GTT TGG GCC
      Thr His Ala Cys Val Pro Thr Asp Pro Asn Pro Gln Glu Val Val
226   ACA CAT GCC TGT GTA CCC ACA GAC CCC AAC CCA CAA GAA GTA GTA
      Leu Gly Asn Val Thr Glu Asn Phe Asn Met Trp Lys Asn Asn Met
271   TTG GGA AAT GTG ACA GAA AAT TTT AAC ATG TGG AAA AAT AAC ATG
      Val Asp Gln Met His Glu Asp Ile Ile Ser Leu Trp Asp Glu Ser
316   GTA GAT CAG ATG CAT GAG GAT ATA ATC AGT TTA TGG GAT GAA AGC
      Leu Lys Pro Cys Val Lys Leu Thr Pro Leu Cys Val Thr Leu Asn
361   CTA AAG CCA TGT GTA AAA TTA ACC CCA CTC TGT GTT ACT TTA AAT
      Cys Thr Asn Leu Asn Ile Thr Lys Asn Thr Thr Asn Pro Thr Ser
406   TGC ACT AAT TTG AAT ATC ACT AAG AAT ACT ACT AAT CCC ACT AGT
      Ser Ser Trp Gly Met Met Glu Lys Gly Glu Ile Lys Asn Cys Ser
451   AGC AGC TGG GGA ATG ATG GAG AAA GGA GAA ATA AAA AAT TGC TCT
      Phe Tyr Ile Thr Thr Ser Ile Arg Asn Lys Val Lys Lys Glu Tyr
496   TTC TAT ATC ACC ACA AGC ATA AGA AAT AAG GTA AAG AAA GAA TAT
      Ala Leu Phe Asn Arg Leu Asp Val Val Pro Ile Glu Asn Thr Asn
541   GCA CTT TTT AAT AGA CTT GAT GTA GTA CCA ATA GAA AAT ACT AAT
      Asn Thr Lys Tyr Arg Leu Ile Ser Cys Asn Thr Ser Val Ile Thr
586   AAT ACT AAG TAT AGG TTA ATA AGT TGT AAC ACC TCA GTC ATT ACA
      Gln Ala Cys Pro Lys Val Ser Phe Gln Pro Ile Pro Ile His Tyr
631   CAG GCC TGT CCA AAG GTA TCC TTT CAG CCA ATT CCC ATA CAT TAT
      Cys Val Pro Ala Gly Phe Ala Met Leu Lys Cys Asn Asn Lys Thr
676   TGT GTC CCG GCT GGG TTT GCG ATG CTA AAG TGT AAC AAT AAG ACA
      Phe Asn Gly Ser Gly Pro Cys Thr Asn Val Ser Thr Val Gln Cys
721   TTC AAT GGA TCA GGA CCA TGC ACA AAT GTC AGC ACA GTA CAA TGT
      Thr His Gly Ile Arg Pro Val Val Ser Thr Gln Leu Leu Leu Asn
766   ACA CAT GGA ATT AGG CCA GTG GTG TCA ACT CAA CTG CTG TTA AAT
      Gly Ser Leu Ala Glu Glu Asp Ile Val Ile Arg Ser Glu Asn Phe
811   GGC AGT CTA GCA GAA GAA GAC ATA GTA ATT AGA TCT GAA AAT TTC
      Thr Asp Asn Ala Lys Thr Ile Ile Val Gln Leu Asn Glu Ser Val
856   ACA GAC AAT GCT AAA ACC ATA ATA GTA CAG CTA AAT GAA TCT GTA
      Val Ile Asn Cys Thr Arg Pro Asn Asn Asn Thr Arg Arg Arg Leu
901   GTA ATT AAT TGT ACA AGA CCC AAC AAC AAT ACA AGA AGA AGG TTA
      Ser Ile Gly Pro Gly Arg Ala Phe Tyr Ala Arg Arg Asn Ile Ile
946   TCT ATA GGA CCA GGG AGA GCA TTT TAT GCA AGA AGA AAC ATA ATA
      Gly Asp Ile Arg Gln Ala His Cys Asn Ile Ser Arg Ala Lys Trp
991   GGA GAT ATA AGA CAA GCA CAT TGT AAC ATT AGT AGA GCA AAA TGG
      Asn Asn Thr Leu Gln Gln Ile Val Ile Lys Leu Arg Glu Lys Phe
1036  AAT AAC ACT TTA CAA CAG ATA GTT ATA AAA TTA AGA GAA AAA TTT
      Arg Asn Lys Thr Ile Ala Phe Asn Gln Ser Ser Gly Gly Asp Pro
1081  AGG AAT AAA ACA ATA GCC TTT AAT CAA TCC TCA GGA GGG GAC CCA
      Glu Ile Val Met His Ser Phe Asn Cys Gly Gly Glu Phe Phe Tyr
1126  GAA ATT GTA ATG CAC AGT TTT AAT TGT GGA GGG GAA TTC TTC TAC
      Cys Asn Thr Ala Gln Leu Phe Asn Ser Thr Trp Asn Val Thr Gly
1171  TGT AAT ACA GCA CAA CTG TTT AAT AGT ACT TGG AAT GTT ACT GGA
      Gly Thr Asn Gly Thr Glu Gly Asn Asp Ile Ile Thr Leu Gln Cys
```

Figure 3A (continued).
Sequence and translation of two cDNAs encoding HIV gp120-CD154 LONG
form extracellular domain fusion proteins.

```
1216  GGG ACA AAT GGC ACT GAA GGA AAT GAC ATA ATC ACA CTC CAA TGC
      Arg Ile Lys Gln Ile Ile Asn Met Trp Gln Lys Val Gly Lys Ala
1261  AGA ATA AAA CAA ATT ATA AAT ATG TGG CAG AAA GTA GGA AAA GCA
      Met Tyr Ala Pro Pro Ile Thr Gly Gln Ile Arg Cys Ser Ser Asn
1306  ATG TAT GCC CCT CCC ATC ACA GGA CAA ATT AGA TGT TCA TCA AAT
      Ile Thr Gly Leu Leu Leu Thr Arg Asp Gly Gly Asn Ser Thr Glu
1351  ATT ACA GGG CTG CTA CTA ACA AGA GAT GGA GGT AAT AGT ACT GAG
      Thr Glu Thr Glu Ile Phe Arg Pro Gly Gly Gly Asp Met Arg Asp
1396  ACT GAG ACT GAG ATC TTC AGA CCT GGA GGA GGA GAT ATG AGG GAC
      Asn Trp Arg Ser Glu Leu Tyr Lys Tyr Lys Val Val Arg Ile Glu
1441  AAT TGG AGA AGT GAA TTA TAT AAA TAT AAA GTA GTA AGA ATT GAA
      Pro Ile Gly Val Ala Pro Thr Arg Ala Lys Arg Arg Thr Val Gln
1486  CCA ATA GGA GTA GCA CCC ACC AGG GCA AAG AGA AGA ACA GTG CAA
      Arg Glu Lys Arg
1531  AGA GAA AAA AGA
```

(Gly₄Ser)₃ linker                                                                  BamHI

```
      Gly Gly Gly Gly Ser Gly Gly Gly Gly Ser Gly Gly Gly Gly Ser Asp Pro
1543  GGG GGA GGC GGT TCA GGA GGT GGA GGT TCT GGA GGT GGC GGA TCG GAT CCA
```

OR ProAspPro linker
BamHI

```
      Pro Asp Pro
1543  CCG GAT CCA
```

CD154 LONG FORM Extracellular Domain

```
1594GS   Arg Arg Leu Asp Lys Ile Glu Asp Glu
1552PDP  AGA AGG TTG GAC AAG ATA GAA GAT GAA
1621GS   Arg Asn Leu His Glu Asp Phe Val Phe Met Lys Thr Ile Gln Arg
1579PDP  AGG AAT CTT CAT GAA GAT TTT GTA TTC ATG AAA ACG ATA CAG AGA
1666GS   Cys Asn Thr Gly Glu Arg Ser Leu Ser Leu Leu Asn Cys Glu Glu
1624PDP  TGC AAC ACA GGA GAA AGA TCC TTA TCC TTA CTG AAC TGT GAG GAG
1711GS   Ile Lys Ser Gln Phe Glu Gly Phe Val Lys Asp Ile Met Leu Asn
1669PDP  ATT AAA AGC CAG TTT GAA GGC TTT GTG AAG GAT ATA ATG TTA AAC
1756GS   Lys Glu Glu Thr Lys Lys Glu Asn Ser Phe Glu Met Gln Lys Gly
1714PDP  AAA GAG GAG ACG AAG AAA GAA AAC AGC TTT GAA ATG CAA AAA GGT
1801GS   Asp Gln Asn Pro Gln Ile Ala Ala His Val Ile Ser Glu Ala Ser
1759PDP  GAT CAG AAT CCT CAA ATT GCG GCA CAT GTC ATA AGT GAG GCC AGC
1846GS   Ser Lys Thr Thr Ser Val Leu Gln Trp Ala Glu Lys Gly Tyr Tyr
1804PDP  AGT AAA ACA ACA TCT GTG TTA CAG TGG GCT GAA AAA GGA TAC TAC
1891GS   Thr Met Ser Asn Asn Leu Val Thr Leu Glu Asn Gly Lys Gln Leu
1849PDP  ACC ATG AGC AAC AAC TTG GTA ACC CTG GAA AAT GGG AAA CAG CTG
1936GS   Thr Val Lys Arg Gln Gly Leu Tyr Tyr Ile Tyr Ala Gln Val Thr
1894PDP  ACC GTT AAA AGA CAA GGA CTC TAT TAT ATC TAT GCC CAA GTC ACC
1981GS   Phe Cys Ser Asn Arg Glu Ala Ser Ser Gln Ala Pro Phe Ile Ala
1939PDP  TTC TGT TCC AAT CGG GAA GCT TCG AGT CAA GCT CCA TTT ATA GCC
2026GS   Ser Leu Cys Leu Lys Ser Pro Gly Arg Phe Glu Arg Ile Leu Leu
1984PDP  AGC CTC TGC CTA AAG TCC CCC GGT AGA TTC GAG AGA ATC TTA CTC
2071GS   Arg Ala Ala Asn Thr His Ser Ser Ala Lys Pro Cys Gly Gln Gln
2029PDP  AGA GCT GCA AAT ACC CAC AGT TCC GCC AAA CCT TGC GGG CAA CAA
2116GS   Ser Ile His Leu Gly Gly Val Phe Glu Leu Gln Pro Gly Ala Ser
2074PDP  TCC ATT CAC TTG GGA GGA GTA TTT GAA TTG CAA CCA GGT GCT TCG
2161GS   Val Phe Val Asn Val Thr Asp Pro Ser Gln Val Ser His Gly Thr
2119PDP  GTG TTT GTC AAT GTG ACT GAT CCA AGC CAA GTG AGC CAT GGC ACT
                                                                    XbaI
2206GS   Gly Phe Thr Ser Phe Gly Leu Leu Lys Leu Glu *** *** Ser Arg
2164PDP  GGC TTC ACG TCC TTT GGC TTA CTC AAA CTC GAG TGA TAA TCT AGA
```

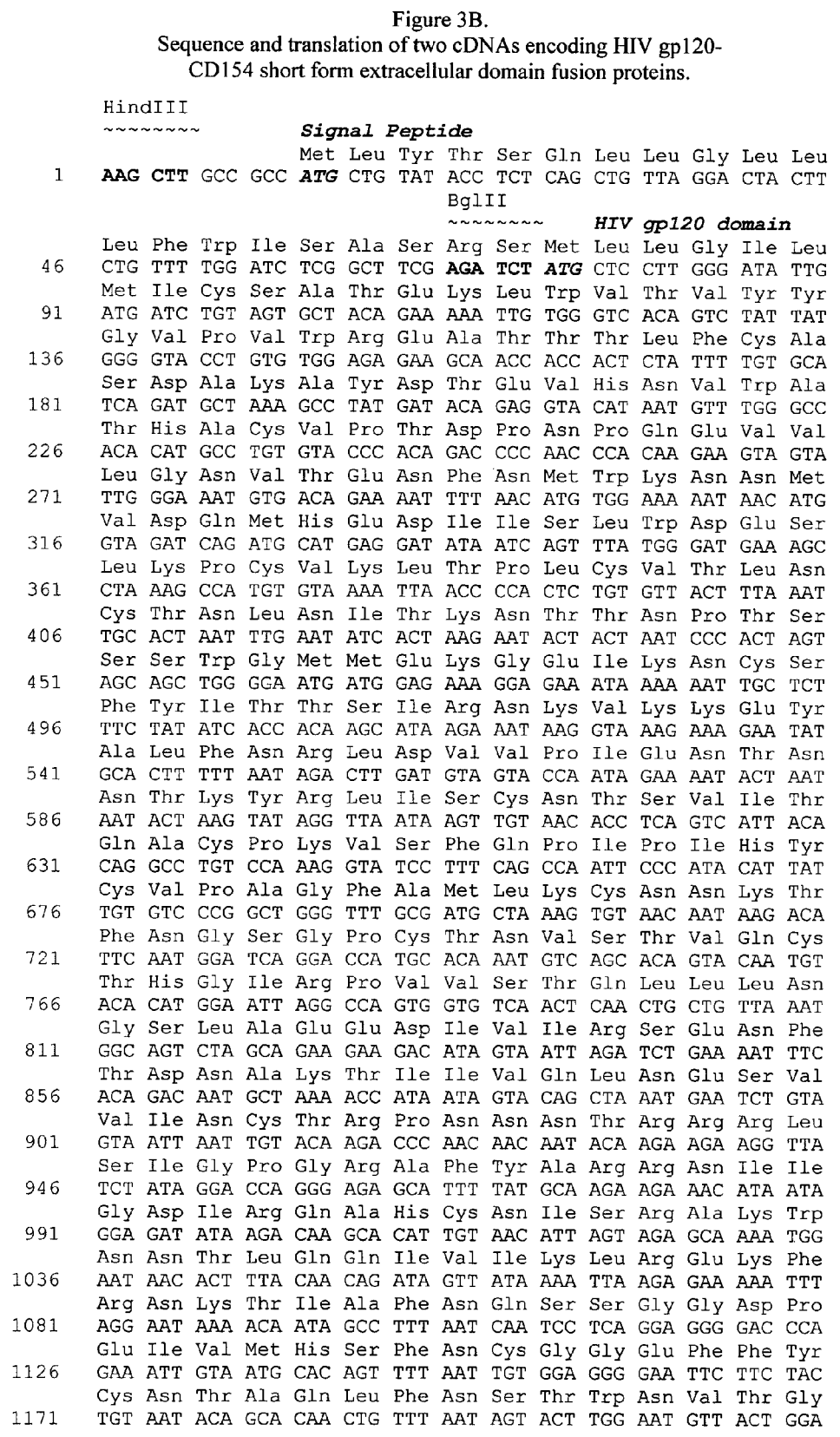

Figure 3B.
Sequence and translation of two cDNAs encoding HIV gp120-
CD154 short form extracellular domain fusion pro Figure 3B (Continued).
Sequence and translation of two cDNAs encoding HIV gp120-
CD154 short form extracellular domain fusion proteins.

DNA VACCINES ENCODING ANTIGEN LINKED TO A DOMAIN THAT BINDS CD40

CROSS REFERENCE TO RELATED APPLICATIONS

This application is entitled to the benefit of Provisional Patent Application Ser. No. 60/159,690, filed 1999 Oct. 14.

BACKGROUND

1. Field of Invention

This invention relates to DNA vaccines, specifically to improved DNA vaccines that induce strong antigen-specific humoral and cellular immune responses.

2. Description of Prior Art

DNA immunization, the inoculation of plasmid DNA encoding a microbial or tumor antigen, is a recent addition to vaccine technology (Donnelly J. J. et al, Ann. Rev. Immunol. 15: 617–648, 1997; Letvin N. L., Science 280: 1875–1879, 1998). Both cellular and humoral immune responses occur after DNA vaccination, and protective immunity against microbial challenge is sometimes induced in experimental animals (Ulmer J. B. et al, Vaccine 12: 1541–1544, 1994; Yokoyama M. et al, J. Virol. 69: 2684–2688, 1995; Xiang Z. Q. et al, Virology 199: 132–140, 1994; Sedegah M. et al, Proc. Natl. Acad. Sci. USA 91: 9866–9870, 1994; Montgomery D. L. et al, DNA Cell Biol. 12: 777–783, 1993). T cell responses, including CD8+ cytotoxic T lymphocyte (CTL) and CD4+ T helper cells, can be stimulated by DNA vaccination in response to antigenic peptides presented by class I and class II MHC molecules (Whitton J. L. et al, Vaccine 17: 1612–1619, 1999). Endogenous protein synthesis allows presentation of foreign antigenic peptides by MHC class I, whereas uptake of soluble protein by APC is required for presentation of peptides by MHC class II. Both arms of the immune response can therefore be induced after DNA vaccination, but the pathways for antigen processing and presentation are distinct for peptides presented by MHC class I or MHC class II. This conclusion is derived from experiments using DNA encoding ubiquitinated protein that is rapidly targeted to intracellular degradation by proteosomes. Ubiquitinated antigen that was degraded so rapidly that intact protein could not leave the cell led to enhanced production of CTL in vivo, but completely eliminated antibody production (Rodriguez F. et al, J. Virol. 71: 8497–8503, 1997; Wu Y. and Kipps T. J., J. Immunol. 159: 6037–6043, 1997). Thus a major limitation of DNA vaccines is their inability to induce strong and sustained humoral immune responses. Strategies for optimization of the cellular immune response to DNA vaccines that do not reduce humoral immune responses are needed.

DNA vaccines for HIV-1 have been tested in animal models and found to induce an immune response that provides protection against challenge only when the virulence of the viral isolate is low. In benign challenge models, chimpanzees were protected from live virus exposure by vaccination with plasmid DNA or by subunit antigens or peptides (Boyer J. D. et al, Nat. Med. 3:526–532, 1997; Kennedy R. C., Nat. Med. 3: 501–502, 1997). However, when highly virulent SIV was tested in rhesus macaques, DNA vaccination was not protective and could only achieve a reduction in virus load even when multiple doses of DNA were inoculated through multiple routes (Lu S. et al, J. Virol. 70: 3978–3991, 1996). Therefore, enhancing the immune response to DNA immunization is an important goal of current AIDS vaccine research. Enhancing the immune response to other DNA vaccines is also desirable in order to provide protection when infected with highly virulent organisms or with a high infectious dose, and to provide long lasting protection. Enhancing the immune response to DNA vaccines encoding tumor antigens is also important for maximizing the anti-tumor response.

One strategy that has been tested is to prime with a DNA vaccine followed by boosting with protein antigen. However, this approach requires construction of multiple vaccines for the same infection or disease, and depends upon multiple injections given in a precise order. It would be desirable to induce protective immunity without needing multiple forms of a vaccine, and without requiring alternating injections of DNA and protein.

Chemical and genetic approaches to enhance the immune response to DNA vaccines have been studied. Chemical adjuvants with some activity include monophosphoryl lipid A (Sasaki S. et al, Infect. Immun. 65: 3520–3528, 1997), saponin QS-21 (Sasaki S et al, J. Virol. 72: 4931–4939, 1998), mannan-coated liposomes (Toda S et al, Immunology 92: 111–117, 1997), and the aminopeptidase inhibitor ubenimex (Sasaki S et al, Clin. Exp. Immunol. 11: 30–36, 1998). Each of these adjuvants modestly enhanced both antibody titers and CTL activity after DNA vaccination in mice. Although the mechanism of action of chemical adjuvants is not fully elucidated, they seem to work by induction of cytokines that amplify responses, by recruitment of macrophages and other lymphoid cells at sites of DNA administration, or by facilitating entry of DNA into host cells (Sasaki S. et al, Anticancer Research 18: 3907–3916, 1998). Several genetic approaches to enhancing responses to DNA vaccines have been tested, including administration of a gene encoding a cytokine (IL2, IL 12, GM-CSF, TCA3, MIP-1$\alpha$) (Chow Y.-H. et al, J. Virol. 71: 169–178, 1997; Hwee Lee A. et al, Vaccine 17: 473–479, 1998; Tsuji T. et al, Immunol. 158: 4008–4014, 1997; Rodriguez D. et al, Gen. Virol. 80: 217–223, 1999; Tsuji T. et al, Immunology 90: 1–6, 1997; Lu Y. et al, Clin. Exp. Immunol. 115: 335–341, 1999) or a costimulatory adhesion receptor (CD86, CD58, CD54) (Tsuji T. et al, Eur. J. Immunol. 27: 782–787, 1997; Kim J. J. et al, J. Clin. Invest. 103: 869–877, 1999; Iwasaki A. et al, J. Immunol. 158: 4591–4601, 1997). Each of these cytokine and adhesion receptor genes increased immune responses to DNA vaccination, with some treatments enhancing CTL generation only, and some enhancing both CTL and antibody production. However, the levels of enhancement of the immune response to DNA vaccination obtained from these approaches are modest and not sustained, so it is important to find additional ways to enhance the immune response to DNA vaccines.

The CD40 receptor must be activated for an effective cellular or humoral immune response after exposure to antigen (Grewal I. S., and Flavell R. A., Annu. Rev. Immunol 16: 111–135, 1998). This conclusion is derived from multiple findings, including the phenotype of patients with hyper IgM (HIGM) syndrome that results from CD154 genetic defects (Aruffo A. et al, Cell 72: 291–300, 1993; Fuleihan R. et al, Proc. Natl. Acad. Sci. USA 90: 2170–2173, 1993; Korthauer U. et al, Nature 361: 539–541, 1993), the phenotype of mice with CD40 or CD154 gene disruption (Grewal I. S. et al, Science 273: 1864–1867, 1996; Kawabe T. et al, Immunity 1: 167–178, 1994; Renshaw B. et al, J. Exp. Med. 180: 1889–1900, 1994; Xu J. et al, Immunity 1: 423–431, 1994), and the effects of actively blocking CD40 in vivo using inhibitory antibodies to CD154 (Durie F. H. et al, Science 261: 1328–1330, 1993; Foy T. M. et al, J. Exp. Med. 178: 1567–1575, 1993; Foy T. M. et al, J. Exp. Med.

180: 157–163, 1994; Durie F. H. et al, J. Clin. Invest. 94: 1333–1338, 1994; Gerritsse K. et al, Proc. Nat. Acad. Sci. USA 93: 2499–2504, 1996). CD40 is expressed in several cell lineages, including B cells, dendritic cells, monocytes, epithelial cells, and endothelial cells. CD40 transmits signals for each of these cell types that regulates activation and differentiation (Hollenbaugh D. et al, EMBO J. 11: 4313–4321, 1992; Kiener P. A. et al, J. Immunol. 155: 4917–4925, 1995; Cella M. et al, J. Exp. Med. 184: 747–752, 1996; Galy A. H., and Spits H., J. Immunol. 152: 775–782, 1992; Clark E. A., and Ledbetter J. A., Proc. Natl. Acad. Sci. USA 83: 4494–4498, 1986). CD40 is activated by crosslinking during cell to cell contact with cells expressing CD40 ligand (CD154), primarily T cells. While soluble forms of CD154 can stimulate CD40, no attempts have been made to use or modify soluble CD154 to promote immune responses to antigens.

CD40 signals to B cells are required for isotype switching and affinity maturation through somatic mutation (Rousset F. et al, J. Exp. Med. 173: 705–710, 1991). In the absence of CD40 signals, germinal centers, the specialized sites of B cell maturation, are not formed, and B cells are unable to differentiate into IgG producing plasma cells (Foy T. M. et al, J. Exp. Med. 180: 157–163, 1994). Patients with HIGM syndrome are not able to form germinal centers or produce IgG antibodies after antigen challenge, and the same phenotype is seen in knockout mice where CD40 or CD154 is not expressed. The CD40 signal has been shown in vitro to promote survival of surface Ig-activated B cells, and to interact with signals from cytokines to induce immunoglobulin isotype switching to IgG, IgA, and IgE production (Holder M. J. et al, Eur. J. Immunol 23: 2368–2371, 1993; Jabara H. H. et al, J. Exp. Med. 177: 925–935, 1990; Grabstein K. H. et al, J. Immunol. 150: 3141–3147, 1993). In addition, HIGM syndrome patients and CD154 knockout mice have impaired lymphocyte proliferation in response to diphtheria toxoid, tetanus, and *Candida*, showing that the CD40 signal is required for T cell priming to protein antigens (Grewal I. S., and Flavell R. A., Annu. Rev. Immunol 16: 111–135, 1998; Toes R. E. M. et al, Sem. Immun. 10: 443–448, 1998; Grewal I. S. et al, Nature 378: 617–620, 1995; Ameratunga R. et al, J. Pediatr. 131: 147–150, 1997; Subauste C. S. et al, J. Immunol. 162: 6690–6700, 1999). Expression of CD154 in vivo to enhance immune responses utilized only the cell surface form of the molecule and resulted in significant toxicity in experimental animals, including induction of lethal autoimmune disease and T cell malignancies (Roskrow M. A et al, Leukemia Research 23: 549–557, 1999; Brown M. P. et al, Nature Medicine 4: 1253–1260, 1998).

In neonates, insufficient stimulation of CD40 due to low levels of expression of CD154 by activated T cells has been identified as a factor in the inability of infants to produce IgG antibodies towards bacterial antigens (Nonoyama S. et al, J. Clin. Invest. 95: 66–75, 1995; Fuleihan R. et al, Eur. J. Immunol. 24: 1925–1928, 1994; Brugnoni D. et al, Eur. J. Immunol. 24: 1919–1924, 1994). This suggests that CD40 signals are not ubiquitous and that highly restricted expression of CD154 may limit the extent of CD40 signaling and thus the magnitude and quality of an immune response. Direct evidence in support of this idea comes from a recent study where a modest increase (1.1–2 fold) in expression of cell surface CD154 in the thymus of mice resulted in a >10 fold increase in the antigen-specific antibody response (Prez-Melgosa M. et al, J. Immunol. 163: 1123–1127, 1999). Some evidence suggests that CD40 stimulation may be deficient in HIV-1 infected individuals, since HIV gp120 suppressed the expression of CD154 by activated T cells in vitro, and production of IL12 is defective in HIV-1 positive individuals (Chirmule N. et al, J. Immunol. 155: 917–924, 1995; Taoufik Y. et al, Blood 89: 2842–2848, 1997; Yoo J. et al, J. Immunol. 157: 1313–1320, 1996; Ito M. et al, AIDS Res. Hum. Retroviruses 14: 845–849, 1998; Benyoucef S. et al, J. Med. Virol. 55: 209–214, 1998). In addition, CD40 stimulation of dendritic cells infected with HIV-1 was found to suppress virus replication, suggesting that transmission of HIV-1 from infected dendritic cells during antigen presentation could be blocked by CD40 signals (McDyer J. F. et al, J. Immunol. 162: 3711–3717, 1999). However, a method for stimulation of CD40 on cells actively presenting antigen to T cells while avoiding toxicity from unregulated CD40 stimulation is needed.

CD40 signals to dendritic cells or B cells causes their differentiation from an antigen uptake function to an antigen processing and presentation function (Sallusto D. et al, J. Exp. Med. 182: 389–400, 1995; Cella M. et al, J. Exp. Med. 184: 747–752, 1996; Faassen A. E. et al, Eur. J. Immunol. 25: 3249–3255, 1995). This shift is accompanied by reduction of the MHC class II intracellular compartment, increased expression of MHC class II on the cell surface, secretion of the Th1 regulatory cytokine IL12 and increased expression of CD86 and CD80. After CD40 activation, dendritic cells and B cells are able to more efficiently present antigen and give a critical costimulatory signal through CD28. The production of IL12 leads to enhanced secretion of IFNγ by T cells and suppression of Th2 cytokine production. The CD40 signal is therefore an important mediator of Th1 cellular immunity and CTL induction. However, selective stimulation of CD40 during antigen presentation is needed to enhance immune responses to vaccination.

In addition to B cells and dendritic cells, CD40 is functionally active on other APC's such as monocytes, where CD40 signals prevent cell death from apoptosis and induce expression of adhesion molecules and production of inflammatory cytokines TNFα and IL8 (Kiener P. A. et al, J. Immunol. 155: 4917–4925, 1995). CD40 has also been reported to be expressed and functionally active on thymic epithelial cells (Galy A. H., and Spits H., J. Immunol. 152: 775–782, 1992) and on many kinds of tumor cells, including carcinomas, melanomas, and lymphomas (Ledbetter J. A. et al, In Leucocyte Typing III: White Cell Differentiation Antigens p. 432–435, 1987; Oxford University Press, Oxford, U.K.; Paulie S. et al, Cancer Immunol. Immunother. 20: 23–28, 1985). In contrast to most normal cells where the CD40 signal enhances survival, in many malignant cells CD40 actively promotes death by apoptosis. Therefore CD40 is functionally active in all cell types that express the receptor, and CD40 signals are central to fundamental processes of survival and differentiation. Because of the widespread expression of functional CD40, localized stimulation of CD40 positive cells that present specific antigen to T cells is desirable so that only APC involved in the specific immune response are activated.

Studies in CD154 knockout mice have confirmed the importance of CD40 activation for the antigen specific priming of T cells. CD154 deficient mice have an enhanced susceptibility to *Leishmania major* and *Toxoplasma gondii* infection, consistent with a central role for CD40 in cellular immunity (Subauste C. S. et al, J. Immunol. 162: 6690–6700, 1999; Campbell K. A. et al, Immunity 4: 283–289, 1996). CTL generation after viral infection in CD154 deficient mice is markedly blunted, and induction of experimental allergic encephalomyelitis (EAE) in response to myelin basic protein does not occur (Grewal I. S. et al, Science 273: 1864–1867, 1996; Grewal I. S. et al, 378: 617–620, 1995). The defect in T cell priming in these models appears to be due to an inability of APC to provide costimulatory signals to T cells (Grewal I. S. et al, Science 273: 1864–1867, 1996; Yang Y. and Wilson J. M., Science 273: 1862–1867, 1996).

Inhibition of CD40 in vivo has been studied in mice using a mAb, MR1, that binds and blocks the CD40 ligand, CD154 (Durie F. H. et al, Science 261: 1328–1330, 1993; Foy T. M. et al, J. Exp. Med. 178: 1567–1575, 1993; Foy T. M. et al, J. Exp. Med. 180: 157–163, 1994; Durie F. H. et al, J. Clin. Invest. 94: 1333–1338, 1994; Gerritsse K. et al, Proc. Nat. Acad. Sci. USA 93: 2499–2504, 1996). These experiments demonstrated that anti-CD154 prevents the induction of autoimmune diseases, including EAE after immunization with myelin basic protein, oophritis after immunization with zona pelucida antigen (ZP3), and spontaneous disease in lupus prone mice (Griggs N. D. et al, J. Exp. Med. 183: 801–807, 1996; Daikh D. I. et al, J. Immunol. 159: 3104–3108, 1997). Anti-CD154 was also effective in preventing both chronic and acute graft versus host (GVH) disease and in preventing rejection of heart allografts after transplantation (Larsen C. P. et al, Nature 381: 434–438, 1996). Thus, CD40 signals are required for T cell responses to antigen, and restriction of the CD40 signal with specific inhibitors is an effective method of limiting T cell priming during an immune response.

The CD40 receptor is therefore a proven target for regulation of antigen specific immunity. While biological inhibitors of CD40 have been studied extensively in mice and in nonhuman primates, there is a need for localized stimulation of CD40 on cells that present antigens to T cells in order to improve the effectiveness of vaccines.

Gp160, the product of the HIV-1 env gene, is cleaved in the Golgi complex into gp120 and gp41 proteins that remain associated through noncovalent interactions. Most neutralizing epitopes of the virus are located on gp120 and gp41, and are expressed by the intact env complex that has been shown to be a trimer (Kwong P. D. et al, Nature 393: 648–659, 1998). Monomeric gp120 can be released from the complex and expose immunodominant epitopes that are non-neutralizing and are located on the internal face of gp120 in the intact trimeric complex (Wyatt R. et al, Nature 393: 705–711, 1998; Broder C. C. et al, PNAS USA 91: 11699–11703, 1994). Thus, stabilization of the env complex is needed for an HIV-1 vaccine in order to preserve conformational epitopes important for neutralization and to mask immunodominant epitopes that are not relevant for neutralization of the env complex.

One attempt to produce a stable, properly folded gp120-gp41 complex was made by altering the cleavage site in gp160 between the gp120 and gp41 domains (Earl P. L. et al, J. Virol. 68: 3015–3026, 1994). By introducing a stop codon before the transmembrane domain of gp41, a soluble molecule composed of gp120 and the extracellular domain of gp41 was produced as a complex that folds properly to bind the CD4 receptor and to express some conformational epitopes. However, this molecule formed dimers and multimers rather than the stable trimers that comprise the native structure of the envelope glycoprotein as revealed in the crystal structure of the gp120 complex.

Three major sites of gp120 have been identified that are involved in cross-neutralization of diverse viral strains (Wyatt R. et al, Nature 393: 705–711, 1998). The V3 domain was found to express linear and conformational epitopes that can be recognized by antibodies that neutralize HIV-1. Although the V3 domain is a variable region, it contains a central portion shared by many HIV-1 isolates, particularly those found in the United States and Europe. The central portion has been called the principle neutralization epitope and is formed from a linear epitope of the amino acid sequence GPGRAF (SEQ ID NO: 28)(Broliden P. A. et al, Proc. Natl. Acad. Sci. USA 89: 461–465, 1992; Broliden P. A. et al, Immunol. 73: 371–376, 1991; Javaherian K. et al, Science 250: 1590–1593, 1990; Javaherian K. et al, Proc. Natl. Acad. Sci. USA 86: 6768–6772, 1989). Conformational epitopes of the V3 loop have also been identified that can be recognized by antibodies that are more broadly neutralizing.

The CD4 binding domain of gp120 is another neutralization site for antibodies directed to HIV-1 env. This domain is a nonlinear, conformational site that depends upon proper folding of gp120 (Kang C.-Y. et al, Proc. Natl. Acad. Sci. USA: 6171–6175, 1991; Lasky L. A. et al, Cell 50: 975–985, 1987). Antibodies can recognize distinct portions of the CD4 binding domain, and may have either type-specific or cross-neutralization properties (Pinter A. et al, AIDS Res. Hum. Retro. 9: 985–996, 1993). Although monomeric gp120 can retain CD4 binding function, a stable trimeric structure of gp120 is thought to be important for masking immunodominant epitopes that are expressed on the internal face of the intact complex (Wyatt R. et al, Nature 393: 705–711, 1998). A third domain of gp120 involved in virus neutralization is exposed upon binding to CD4, and functions to bind the chemokine coreceptor to allow virus entry into the cell (Rizzuto C. D. et al, Science 280: 1949–1953, 1998). Thus a stable trimer of HIV-1 env is needed to present the major cross-neutralization epitopes and to prevent exposure of internal, immunodominant epitopes that do not induce neutralizing antibodies.

CD154 is a TNF-related, type II membrane protein that forms stable trimers (Mazzei G. J. et al, J. Biol. Chem. 270: 7025–7028, 1995). Soluble fusion proteins of human CD154 have been expressed using murine CD8 at the amino terminal side of the CD154 molecule (Hollenbaugh D. et al, EMBO J. 11: 4313–4321, 1992). Single chain Fv (scFv) molecules have also been constructed using heavy and light chain variable regions cloned from the G28-5 hybridoma that produces antibody specific for human CD40 (Ledbetter J. A. et al, Crit. Rev. Immunol. 17: 427–435, 1997). Both CD154 and G28-5 scFv fusion proteins retain functional activity as soluble molecules in vitro. However, no use of these molecules to improve the effectiveness of vaccines has been found.

SUMMARY

For vaccines to be effective, they must induce both humoral and cellular immune responses. This invention describes improved vaccines that target antigens to cell surface receptors. DNA vaccines are a recent addition to immunization technology. However, further optimization of DNA vaccines is needed to induce long-lasting protection against tumor antigens, virulent HIV-1 isolates, and other pathogenic microorganisms. Receptor activation and targeting improves the ability of DNA vaccines to generate strong cellular immunity and high titers of neutralizing antibodies. CD40 is a preferred receptor for targeting and activation. DNA vaccines encoding CD40 ligand (CD154) or a single chain Fv (scFv) specific for CD40, fused with DNA encoding portions of the HIV-1 env protein are preferred embodiments of the invention. A molecule comprising the extracellular domain of HIV-1env gp160 or env gp120 linked to the extracellular domain of CD154 is a stable trimer that improves immune recognition of HIV-1 env cross-neutralization epitopes. After DNA vaccination, the expression of the fusion protein in vivo results in both activation of the CD40 receptor and direction of HIV-1 env antigens into the endocytic pathway of CD40 positive antigen presenting cells (APC). Internalization of env antigens after binding the CD40 receptor enhances presentation of peptides by MHC molecules. Activation of the CD40 receptor promotes B cell and APC maturation leading to effective antibody production and generation of CD4+ helper T cell and CD8+ CTL activity. The combination of CD40 activation, stabilization of the HIV-1 gp160 or gp120 env trimer, and enhanced presentation of antigenic peptides by MHC molecules thus improves immune responses to HIV-1 antigens. Protein molecules of the invention can be injected directly into mammals or encoded by DNA vaccines.

DRAWINGS

FIG. 1.

Schematic representation of fusion proteins that target antigen to cell surface receptors expressed by antigen presenting cells.
- A. A fusion protein expressed from a cDNA construct that encodes an antigen domain attached with a linker to a receptor targeting domain. The antigen domain may be attached to the amino terminus of the receptor targeting domain as shown, or may be attached to the carboxy terminus of the receptor targeting domain.
- B. A fusion protein expressed from a cDNA construct that encodes the HIV env antigen or a subdomain, is attached to the amino terminus of the CD154 extracellular domain.
- C. A fusion protein expressed from a cDNA construct that encodes the HIV env antigen or a subdomain, is attached to the amino terminus of a single chain Fv specific for CD40.
- D. A fusion protein expressed from a cDNA construct as in C, except that the scFv that binds CD40 is oriented with the light chain variable region ($V_L$) attached to the carboxy-terminus of the heavy chain variable region ($V_H$).
- E. A fusion protein expressed from a cDNA construct that encodes the HIV env antigen or a subdomain, is attached to a camelid variable region ($V_{HH}$) that binds CD40.
- F. A fusion protein expressed from a cDNA construct that encodes the HIV env antigen or a subdomain, is attached to a peptide that binds CD40.

FIG. 2.

A. Sequence of two cDNAs encoding HIV gp120-V3 loop/CD154 long form extracellular domain fusion proteins.

The sequence of a cDNA construct and corresponding fusion protein encoding the HIV V3 loop from gp120 with a (ProAspPro) linker (SEQUENCE ID NO.: 17 [DNA] OR SEQUENCE ID NO.: 25 [FUSION PROTEIN]) or a (Gly$_4$Ser)$_3$ (SEQ ID NO: 29) linker (SEQ. ID NO.: 16 [DNA] OR SEQ. ID NO.:24 [FUSION PROTEIN]) fused to the CD154 extracellular domain encoded between amino acids 48 (Arg)–261(Leu), with an additional (Glu) residue at the carboxyl end of the protein, not present in wild type CD154. The sequence of the fusion protein is indicated using the three-letter amino acid code convention, above each codon of the open reading frame. Relevant restriction sites are indicated on the drawing and the nucleotides encoding sites at domain fusion junctions are displayed in boldface type, while the first codon of each fused domain is indicated in underlined, italicized type. The protein domains are labeled above the relevant position in the sequence. The nucleotide number is indicated in the left margin with a designation for the PDP linker form or the G4S linker form.

B. Sequence of two cDNAs encoding HIV V3 loop-CD154 short form extracellular domain fusion proteins.

The two HIV V3 loop constructs with alternate linkers, either (ProAspPro) (SEQUENCE ID NO.: 19 [DNA] OR SEQUENCE ID NO.: 27 [FUSION PROTEIN]) or (Gly$_4$Ser)$_3$ (SEQ ID NO: 29) linker (SEQUENCE ID NO.: 18 [DNA] OR SEQUENCE ID NO.: 26 [FUSION PROTEIN]) were also fused to the short form of the CD154 extracellular domain encoded from amino acids 108 (Glu)–261 (Leu) plus an extra glutamic acid residue at the carboxy terminus, not encoded by wild type CD154. All sequences are labeled as described for FIG. 2A.

FIG. 3.

A. Sequence of two HIV gp120env-CD154 long form extracellular domain cDNA and the predicted fusion proteins.

The sequence of a cDNA construct and corresponding fusion protein encoding the HIV gp120 with a (ProAspPro) linker (SEQ. ID NO.: 13 [DNA] OR SEQ. ID NO.: 21 [FUSION PROTEIN]) or a (Gly$_4$Ser)$_3$ (SEQ ID NO: 29) linker (SEQ. ID NO.: 12 [DNA] OR SEQ. ID NO.: 20 [FUSION PROTEIN]) fused to the CD154 extracellular domain (Long Form) encoded between amino acids 48 (Arg)–261(Leu)+(Glu). All sequences are labeled as described for FIG. 2A.

B. Sequence of two HIV gp120env-CD154 short form extracellular domain cDNAs and the predicted fusion proteins.

The sequence of a cDNA construct and corresponding fusion protein encoding the HIV gp120 with a (ProAspPro) linker (SEQ. ID NO.: 15 [DNA] or SEQ. ID NO.: 23 [fusion protein]) or a (Gly4Ser)3 (SEQ ID NO: 29) linker (SEQ. ID NO.: 14 [DNA] or SEQ. ID NO.: 22 [fusion protein]) fused to the short form of the CD154 extracellular domain encoded between amino acids 108 (Glu)–261 (Leu)+(Glu). All sequences are labeled as described for FIG. 2A.

DESCRIPTION

This invention relates to improved vaccines comprising one or more antigens attached to a domain that targets at least one cell surface receptor. The vaccine may be delivered either as a protein, as a DNA plasmid, or by a viral vector. The expression of the DNA after injection of the plasmid or viral vector in vivo results in the secretion of the antigen(s) attached to a targeting domain, directing the antigen(s) to a cell surface receptor. Receptor-mediated internalization of the antigen into the endocytic compartment of cells that express the receptor enhances the presentation of antigenic peptides by MHC class II molecules that circulate through this compartment. Presentation of antigenic peptides by MHC class I molecules is mediated by the cells expressing the DNA vaccine, and is enhanced in cells that internalize the antigen-targeting domain fusion protein by movement of the fusion protein from the endocytic compartment into the cytoplasm. The activation of antigen-specific CD4+ T cells and CD8+ T cells is increased, resulting in better humoral and cellular immune responses.

The preferred receptor(s) chosen for antigen targeting are those expressed by antigen presenting cells (APC), such as dendritic cells. Desirable receptors for targeting include but are not limited to CD80, CD86, CD83, CD40, CD32, CD64, Flt3, Dec 205, and ICOS ligand. The CD40 receptor is a preferred receptor for antigen targeting, since signals from CD40 regulate activation and differentiation of APC. Fusion proteins of antigen and CD154 (CD40 ligand) combine the functions of antigen targeting and activation of APC by simultaneous delivery of CD40 signals.

The preferred antigen(s) for receptor targeting are HIV-1 and HIV-2 viral antigens, since vaccines have not been effective in protecting against virulent viral isolates. Attachment of HIV-1 gp160 or gp120 extracellular domain to CD154 extracellular domain stabilizes the trimeric structure of HIV-1 env. However, the invention is not limited to HIV env antigens, since improved immune responses to vaccines are needed to provide long-lasting protection against infection with high doses of pathogenic microorganisms or against tumors.

Thus the structure of the invention's main embodiment is a DNA plasmid encoding the extracellular domain of HIV-1 env gp160 attached to the CD154 extracellular domain.

The fusion protein expressed from this DNA plasmid a) stabilizes the trimeric structure of HIV-1 env, b) directs the HIV-1 antigen into the MHC class II compartment of CD40 positive cells, and c) selectively activates the CD40 receptor to increase APC functional activity.

The main embodiment of the invention encodes a stable trimer that expresses the major cross-neutralization epitopes of HIV-1 env while masking the internal env epitopes that are not involved in virus neutralization. Antigenic peptides of HIV env are presented by MHC class I molecules by cells that express the DNA, while antigenic peptides of HIV env are presented by MHC class II molecules in CD40 positive cells that internalize the trimeric antigen-CD154 fusion protein. Activation of the CD40 receptor on cells bound by the antigen-CD154 fusion protein increases the specific immune response due to increased production of IL12 and increased expression of costimulatory molecules CD80 and CD86.

OPERATION

An improved DNA vaccine for AIDS comprising the extracellular domain of HIV-1 gp160, HIV-1 gp120, or a subdomain of these antigens fused to the extracellular domain of CD154 is described. Alternative embodiments of the invention use a smaller portion of the CD154 molecule composed of an 18 kDa subunit from Glu-108 to Leu-261 (Mazzei G. J. et al, J. Biol. Chem. 270: 7025–7028, 1995). The extracellular domain of gp160 can also be shortened by removing the gp41 domain, removing the V1 and V2 domains, or mutating the glycosylation sites without damaging the conformational structure of the HIV-1 envelope (Kwong P. D. et al, Nature 393: 648–659, 1998). These changes could further improve the activity of the vaccine, since the V1 and V2 loops, and the carbohydrate structures are thought to be exposed, clade specific epitopes that prevent or dilute the immune response to important cross-neutralization epitopes for diverse clades of HIV-1. Linkers between gp160 and CD154 can also be used. Thus, alternative embodiments of the invention minimize the CD154 domain, remove gp41, V1, V2, or glycosylation sites of gp160. This invention also envisions DNA vaccines comprising other HIV-1 antigens and antigens from alternative isolates of HIV-1, fused to the extracellular domain of CD154.

Delivery of antigen(s) to the CD40 receptor may use anti-CD40 scFv instead of CD154. Single antibody variable regions ($V_{HH}$) or peptides that bind CD40 are also included in the scope of the invention.

Antigen targeting to receptors is not limited to the CD40 receptor. Alternative receptors preferred for targeting include CD80, CD86, Dec205, ICOS ligand, Flt 3, Fc receptors, and CD83. All cell surface receptors are envisioned by this invention. Receptors may be targeted by ligands, scFv molecules, single variable regions or peptides. Additional methods of attachment of antigen(s) to receptor targeting domains are envisioned, including chemical linkages of subunits, disulfide bonds, or noncovalent attachments such as leucine zipper motifs and the like. The invention contemplates injection of protein, injection of DNA plasmids, or viral vectors encoding the molecules comprising one or more antigens linked to a receptor-binding domain.

Antigens targeted to cell surface receptors are not limited to HIV gp160 antigens. Other antigens, including tumor antigens, parasite antigens, bacterial antigens, and viral antigens are included in the scope of the invention.

The invention also envisions delivery of antigens to cell surface receptors in order to induce antigen-specific tolerance or nonresponsiveness. For this application, an autoantigen would be chosen and the vaccine would be used to treat autoimmune disease.

The invention also envisions antigen(s) that are natural components of the body, such as tumor-associated antigens, where an immune response to the antigen(s) breaks tolerance to the antigen, resulting in a change in immune homeostasis.

The following examples describe particular embodiments of the invention but are not meant to limit its scope.

EXAMPLE 1

A preferred embodiment of the DNA vaccine includes an amino-terminal secretory signal peptide sequence upstream and adjacent to a cDNA sequence cassette encoding the desired antigen. This molecule is then fused to the extracellular domain of CD154 or to a portion of the extracellular domain of CD154 which retains the ability to bind CD40, or to an scFv targeted to CD40, to create a fusion protein expression cassette that targets the antigen to the antigen presenting cell through the CD40 receptor as diagrammed in FIG. 1. The expression cassette is inserted into an appropriate mammalian expression vector or virus to achieve high level expression of the fusion protein either in vitro or in vivo.

The leader peptide is encoded on complementary oligonucleotides with a single-stranded HindIII cohesive end at the 5' terminus, and a BglII cohesive end at the 3' terminus. The sense oligonucleotide is designated SEQUENCE ID NO: 1 or HBLPS and the sequence is as follows:

5'agcttgccgccatgctgtataccctct-
cagctgttaggactacttctgttttggatctcggcttcga-3'.

The antisense oligonucleotide is designated SEQUENCE ID NO: 2 or HBLPAS and the sequence is as follows:

5'gatctcgaagcccgagatccaaaaca-
gaagtagtcctaacagctgagaggtatacagcatggcggca-3'. The two molecules anneal to one another except at the overhanging nucleotides indicated in boldface type. Alternative embodiments could include other secretory signal peptides or localization sequences.

The extracellular domain of human CD154 was PCR amplified using cDNA generated with random primers and RNA from human T lymphocytes activated with PHA (phytohemagglutinin). Two different fusion junctions were designed which resulted in a short or truncated form (form S4) including amino acids 108 (Glu)–261 (Leu)+(Glu), and a long or complete form (form L2) including amino acids 48 (Arg)–261 (Leu)+(Glu), of the extracellular domain of CD154. The sense primer which fuses the extracellular domain to the targeted antigen includes a BamHI site for cloning that introduces the peptide sequence PDP or (ProAspPro) at the fusion junction and can also encode a linker peptide such as (Gly$_4$Ser)$_3$ (SEQ ID NO: 29) to separate the antigen from the extracellular domain. The oligonucleotide primers used in amplifying the short form (S4) of the CD154 extracellular domain encoding amino acids 108 (Glu)–261 (Leu)+(Glu) are as follows:

The sense primer is designated SEQUENCE ID NO: 3 or CD154BAM108 and encodes a 34 mer with the following sequence: 5'-gtt gtc gga tcc aga aaa cag ctt tga aat gca a-3', while the antisense primer is designated SEQUENCE ID NO: 4 or CD154XBA and encodes a 44 mer with the following sequence: 5'-gtt gtt tct aga tta tca ctc gag ttt gag taa gcc aaa gga cg-3'.

The oligonucleotide primers used in amplifying the long form (L2) of the CD154 extracellular domain encoding amino acids 48 (Arg)-261 (Leu)+(Glu), are as follows: The sense primer is identified as SEQUENCE ID NO: 5 or CD154 BAM48 and encodes a 35 mer with the following sequence: 5'-gtt gtc gga tcc aag aag gtt gga caa gat aga ag-3', while the antisense primer is also SEQUENCE ID NO: 4 or CD154XBA encoding the 44 mer: 5'-gtt gtt tct aga tta tca ctc gag ttt gag taa gcc aaa gga cg-3'.

A variety of different antigens can be encoded on cDNA cassettes to be inserted between the leader peptide cassette and the CD40 targeted domain (such as a truncated or complete CD154 extracellular domain or a CD40 specific scFv). In a preferred embodiment of the invention, the cDNA antigen encoded by the vaccine is the HIV-1 gp120 or a fragment of this antigen, such as the V3 loop. The primer sets used to amplify the complete gp120 domain include the sense primer SEQUENCE ID NO: 6 or GP120Bgl2f 5'-gga tat tga tga gat cta gtg cta cag-3' and one of two antisense primers encoding different linkers. Either the antisense primer encoding the ProAspPro linker, identified as SEQUENCE ID NO: 7 or GP120PDPr 5'-gaa cac agc tcc tat tgg atc cgg tct ttt ttc tct ttg cac-3' or the antisense primer encoding the (Gly$_4$Ser)$_3$ (SEQ ID NO: 29) linker, identified as SEQUENCE ID NO: 8 or GP120G4Sr 5'-cct gca tgg atc cga tcc gcc acc tcc aga acc tcc acc tcc tga acc gcc tcc ccc tct ttt ttc tct ttg cac tgt tct tct ctt tgc-3' were used to amplify the gp120 domain with the desired linker attached. PV75 Kgp160(89.6) DNA was used as template in PCR reactions. Alternatively, other isolates or sequence variants of gp120 or gp160 are available and can be substituted to create novel fusion cassettes. PCR amplification reactions were performed using cloned plasmid DNA as template (approximately 45 ng), 3 mM MgCl$_2$, 0.3 MM dNTPs, 1/10 volume 10× reaction buffer supplied by the manufacturer, 10 pmol sense primer, 10 pmol antisense primer, and 2.5 units TAQ polymerase (Takara Pharmaceuticals) in a total reaction volume of 50 □l. The amplification profile included an initial 4 minute 94° C. denaturation, followed by a 30 cycle program of 50° C. annealing for 30 seconds, 72° C. extension for 30 seconds, and 94° C. denaturation for 30 seconds. PCR fragments were purified by ethanol precipitation, resuspended in 30 □l ddH$_2$O and 10 □l was digested with BglII (Roche) restriction endonuclease in a 20 □l reaction volume at 37° C. for 3 hours. Fragments were gel purified, purified using QIAEX kits according to the manufacturer's instructions (QIAGEN, San Diego, Calif.), and ligated along with the annealed leader peptide oligonucleotides to HindIII-BamHI digested expression vector already containing the CD154 extracellular domain as a BamHI-XbaI fragment. Recombinant clones were screened for the correct orientation and presence of inserts, and the resulting positive clones were verified by DNA sequencing using an ABI 310 sequence analyzer and the ABI Prism Dye Terminator Reaction Chemistry. The final fusion cassette encodes the synthetic leader peptide fused to the HIV gp120 domain with either a (ProAspPro) linker or a (Gly$_4$Ser)$_3$ (SEQ ID NO: 29) linker, and then to the CD154 extracellular domain long (FIG. 3A) or short (FIG. 3B) form to create the embodiments of example 1.

EXAMPLE 2

In an alternative preferred embodiment, the V1 and V2 domains of gp120 are removed and only the V3 loop domain from HIV gp120 is encoded on a BglII-BamHI fragment and fused to the signal peptide and the CD154 extracellular domain to create the vaccine, as illustrated in FIGS. 2A and B. This antigen domain is separated from the CD154 short (FIG. 2B) or long extracellular domain (FIG. 2A) by a peptide linker encoding the amino acids (ProAspPro), or a longer peptide linker encoding the amino acids (Gly$_4$Ser)$_3$ (SEQ ID NO: 29).

The V3 loop was PCR amplified from pV75 (gp 89.6), a plasmid containing HIV gp120 from isolate LAV, using the following primer set:

The antisense primer encoding a ProAspPro linker is SEQUENCE ID NO: 9 or V3PDPr

5'-gtt att cca tgg atc cgg act aat ctt aca atg tgc ttg-3'

The sense primer fusing the antigen to the signal peptide is SEQUENCE ID NO: 10 or V3Bgl2f 5'-gta cag cta aat aga tct gta gta att aat tg-3'

The antisense primer encoding a (Gly$_4$Ser)$_3$ (SEQ ID NO: 29) linker is SEQUENCE ID NO: 11 or V3G4Sr 5'-ggt gca tgg atc cga acc tcc acc gcc aga tcc acc gcc tcc tga ggc acc gcc acc act aat gtt aca atg tgc ttg ttg tct tat atc tcc-3'.

Amplification, digestion, purification, and ligation conditions were identical to those described above for the full-length gp120 domain. The final fusion cassettes encode the HIV gp120-V3 loop with either a (ProAspPro) linker or a (Gly$_4$Ser)$_3$ (SEQ ID NO: 29) linker fused to either the CD154 extracellular domain as diagrammed in FIG. 2A for the long form, and FIG. 2B for the short form of the CD40 binding domain.

Other antigens and linkers can be substituted to create alternative vaccines by construction of the appropriate cDNA cassettes encoding the desired domains and attaching them to the CD154 extracellular domain. Because of the high degree of sequence variation among HIV isolates, alternative sequences might be incorporated as needed to target particular clades. Other viral antigens such as HIV tat or their subdomains can be substituted for the HIV domains described here. Similarly, an alternate APC targeted domain can be substituted for the CD40 binding domain, such as a domain which binds to CD80 or CD86, or to ICOS ligand, or to one of several other cell surface receptors expressed on antigen presenting cells. Surface receptors that internalize readily are preferred over receptors that contain multiple transmembrane domains and do not internalize readily such as G-protein coupled chemokine receptors.

We claim:

1. An antigenic polypeptide comprising an antigen domain and a receptor-binding domain, said antigen domain comprising HIV-1 gp160 or a portion thereof and said receptor-binding domain comprising a CD40-binding polypeptide, wherein the CD40-binding polypeptide is selected from the group consisting of CD154, extracellular domains of CD154 or a portion of the extracellular domain which retains the ability to bind CD40, anti-CD40 scFv, and single antibody variable regions that bind CD40.

2. An antigenic polypeptide of claim 1, wherein said receptor-binding domain comprises at least a portion of an immunoglobulin.

3. An antigenic polypeptide of claim 1, wherein said receptor-binding domain comprises a single chain Fv.

4. An antigenic polypeptide of claim 1, wherein said CD-40 binding protein comprises CD154 or a portion of CD154.

5. An antigenic polypeptide of claim 1, comprising an amino acid sequence according to any one of SEQ ID NO: 20, 21, 22, 23, 24, 25, 26, or 27.

6. An antigenic polypeptide of claim 1, wherein said CD40-binding polypeptide comprises a camelid immunoglobulin variable region.

7. An antigenic polypeptide of claim 1, wherein said receptor-binding domain is capable of binding CD40 and one or more additional receptors.

8. An antigenic polypeptide of claim 1, encoded by a polynucleotide comprising a sequence according to any one of SEQ ID NO: 12, 13, 14, 15, 16, 17, 18, or 19.

9. An antigenic polypeptide of claim 8, wherein said polynucleotide is operably linked to a DNA plasmid.

10. An antigenic polypeptide of claim 1 that is capable of eliciting an immune response in an animal.

11. An antigenic polypeptide of claim 1 that is produced in an animal.

12. An antigenic polypeptide comprising an antigen domain and a receptor-binding domain, said antigen domain comprising HIV-1 gp160 or a portion of HIV-1 gp160, said receptor-binding domain comprising at least a portion of a CD154 polypeptide capable of binding to CD40.

13. An antigenic polypeptide of claim 12 encoded by a polynucleotide comprising a sequence according to any one of SEQ ID NO: 12, 13, 14, 15, 16, 17, 18, or 19.

14. An antigenic polypeptide of claim 12 wherein said antigenic polypeptide comprises an amino acid sequence according to any one of SEQ ID NO: 20, 21, 22, 23, 24, 25, 26, or 27.

* * * * *

SEQUENCE LISTING

<160> NUMBER OF SEQ ID NOS: 29

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agcttgccgc catgctgtat acctctcagc tgttaggact acttctgttt tggatctcgg    60
cttcga                                                               66

<210> SEQ ID NO 2
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatctcgaag cccgagatcc aaaacagaag tagtcctaac agctgagagg tatacagcat    60
ggcggca                                                              67

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 3
gttgtcggat ccagaaaaca gctttgaaat gcaa                                34

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 4
gttgtttcta gattatcact cgagtttgag taagccaaag gacg                     44

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 5
gttgtcggat ccaagaaggt tggacaagat agaag                               35

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 6

-continued

```
ggatattgat gagatctagt gctacag                                          27

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 7
gaacacagct cctattggat ccggtctttt ttctctttgc ac                         42

<210> SEQ ID NO 8
<211> LENGTH: 90
<212> TYPE: DNA
<213> ORGANISM: Artificial Sequence
<220> FEATURE:
<223> OTHER INFORMATION: Description of Artificial Sequence: Primer

<400> SEQUENCE: 8
cctgcatgga tccgatccgc cacctccaga acctccacct cctgaaccgc ctccccctct     60
tttttctctt tgcactgttc ttctctttgc                                       90

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 9
gttattccat ggatccggac taatcttaca atgtgcttg                             39

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 10
gtacagctaa atagatctgt agtaattaat tg                                    32

<210> SEQ ID NO 11
<211> LENGTH: 93
<212> TYPE: DNA
<213> ORGANISM: Artificial Sequence
<220> FEATURE:
<223> OTHER INFORMATION: Description of Artificial Sequence: Primer

<400> SEQUENCE: 11
ggtgcatgga tccgaacctc caccgccaga tccaccgcct cctgaggcac cgccaccact     60
aatgttacaa tgtgcttgtt gtcttatatc tcc                                   93

<210> SEQ ID NO 12
<211> LENGTH: 2252
<212> TYPE: DNA
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: CDS
<222> LOCATION: (13)..(2238)
<220> FEATURE:
```

```
<221> NAME/KEY: sig_peptide
<222> LOCATION: (13)..(72)
<220> FEATURE:
<221> NAME/KEY: mat_peptide
<222> LOCATION: (73)..(2238)
<220> FEATURE:
<221> NAME/KEY: misc_feature
<222> LOCATION: (73)..(1587)
<223> OTHER INFORMATION: HIV gp120 allele + (Gly4Ser)3 linker
<220> FEATURE:
<221> NAME/KEY: misc_feature
<222> LOCATION: (1594)..(2238)
<223> OTHER INFORMATION: CD154 extracellular domain from amino acids
      48-261 + Glu binds to CD40

<400

-continued

```
                220                 225                 230
gga att agg cca gtg gtg tca act caa ctg ctg tta aat ggc agt cta      819
Gly Ile Arg Pro Val Val Ser Thr Gln Leu Leu Leu Asn Gly Ser Leu
        235                 240                 245 gca gaa gaa gac ata gta att aga tct gaa aat ttc aca gac aat gct      867
Ala Glu Glu Asp Ile Val Ile Arg Ser Glu Asn Phe Thr Asp Asn Ala
250                 255                 260                 265 aaa acc ata ata gta cag cta aat gaa tct gta gta att aat tgt aca      915
Lys Thr Ile Ile Val Gln Leu Asn Glu Ser Val Val Ile Asn Cys Thr
                        270                 275                 280 aga ccc aac aac aat aca aga aga agg tta tct ata gga cca ggg aga      963
Arg Pro Asn Asn Asn Thr Arg Arg Arg Leu Ser Ile Gly Pro Gly Arg
                285                 290                 295 gca ttt tat gca aga aga aac ata ata gga gat ata aga caa gca cat     1011
Ala Phe Tyr Ala Arg Arg Asn Ile Ile Gly Asp Ile Arg Gln Ala His
            300                 305                 310 tgt aac att agt aga gca aaa tgg aat aac act tta caa cag ata gtt     1059
Cys Asn Ile Ser Arg Ala Lys Trp Asn Asn Thr Leu Gln Gln Ile Val
        315                 320                 325 ata aaa tta aga gaa aaa ttt agg aat aaa aca ata gcc ttt aat caa     1107
Ile Lys Leu Arg Glu Lys Phe Arg Asn Lys Thr Ile Ala Phe Asn Gln
330                 335                 340                 345 tcc tca gga ggg gac cca gaa att gta atg cac agt ttt aat tgt gga     1155
Ser Ser Gly Gly Asp Pro Glu Ile Val Met His Ser Phe Asn Cys Gly
                        350                 355                 360 ggg gaa ttc ttc tac tgt aat aca gca caa ctg ttt aat agt act tgg     1203
Gly Glu Phe Phe Tyr Cys Asn Thr Ala Gln Leu Phe Asn Ser Thr Trp
                365                 370                 375 aat gtt act gga ggg aca aat ggc act gaa gga aat gac ata atc aca     1251
Asn Val Thr Gly Gly Thr Asn Gly Thr Glu Gly Asn Asp Ile Ile Thr
            380                 385                 390 ctc caa tgc aga ata aaa caa att ata aat atg tgg cag aaa gta gga     1299
Leu Gln Cys Arg Ile Lys Gln Ile Ile Asn Met Trp Gln Lys Val Gly
        395                 400                 405 aaa gca atg tat gcc cct ccc atc aca gga caa att aga tgt tca tca     1347
Lys Ala Met Tyr Ala Pro Pro Ile Thr Gly Gln Ile Arg Cys Ser Ser
410                 415                 420                 425 aat att aca ggg ctg cta cta aca aga gat gga ggt aat agt act gag     1395
Asn Ile Thr Gly Leu Leu Leu Thr Arg Asp Gly Gly Asn Ser Thr Glu
                        430                 435                 440 act gag act gag atc ttc aga cct gga gga gga gat atg agg gac aat     1443
Thr Glu Thr Glu Ile Phe Arg Pro Gly Gly Gly Asp Met Arg Asp Asn
                445                 450                 455 tgg aga agt gaa tta tat aaa tat aaa gta gta aga att gaa cca ata     1491
Trp Arg Ser Glu Leu Tyr Lys Tyr Lys Val Val Arg Ile Glu Pro Ile
            460                 465                 470 gga gta gca ccc acc agg gca aag aga aga aca gtg caa aga gaa aaa     1539
Gly Val Ala Pro Thr Arg Ala Lys Arg Arg Thr Val Gln Arg Glu Lys
        475                 480                 485 aga ggg gga ggc ggt tca gga ggt gga ggt tct gga ggt ggc gga tcg     1587
Arg Gly Gly Gly Gly Ser Gly Gly Gly Gly Ser Gly Gly Gly Gly Ser
490                 495                 500                 505 gat cca aga agg ttg gac aag ata gaa gat gaa agg aat ctt cat gaa     1635
Asp Pro Arg Arg Leu Asp Lys Ile Glu Asp Glu Arg Asn Leu His Glu
                        510                 515                 520 gat ttt gta ttc atg aaa acg ata cag aga tgc aac aca gga gaa aga     1683
Asp Phe Val Phe Met Lys Thr Ile Gln Arg Cys Asn Thr Gly Glu Arg
                525                 530                 535 tcc tta tcc tta ctg aac tgt gag gag att aaa agc cag ttt gaa ggc     1731
```

-continued

```
Ser Leu Ser Leu Leu Asn Cys Glu Glu Ile Lys Ser Gln Phe Glu Gly
        540                 545                 550 ttt gtg aag gat ata atg tta aac aaa gag gag acg aag aaa gaa aac     1779
Phe Val Lys Asp Ile Met Leu Asn Lys Glu Glu Thr Lys Lys Glu Asn
    555                 560                 565 agc ttt gaa atg caa aaa ggt gat cag aat cct caa att gcg gca cat     1827
Ser Phe Glu Met Gln Lys Gly Asp Gln Asn Pro Gln Ile Ala Ala His
570                 575                 580                 585 gtc ata agt gag gcc agc agt aaa aca aca tct gtg tta cag tgg gct     1875
Val Ile Ser Glu Ala Ser Ser Lys Thr Thr Ser Val Leu Gln Trp Ala
                590                 595                 600 gaa aaa gga tac tac acc atg agc aac aac ttg gta acc ctg gaa aat     1923
Glu Lys Gly Tyr Tyr Thr Met Ser Asn Asn Leu Val Thr Leu Glu Asn
            605                 610                 615 ggg aaa cag ctg acc gtt aaa aga caa gga ctc tat tat atc tat gcc     1971
Gly Lys Gln Leu Thr Val Lys Arg Gln Gly Leu Tyr Tyr Ile Tyr Ala
        620                 625                 630 caa gtc acc ttc tgt tcc aat cgg gaa gct tcg agt caa gct cca ttt     2019
Gln Val Thr Phe Cys Ser Asn Arg Glu Ala Ser Ser Gln Ala Pro Phe
    635                 640                 645 ata gcc agc ctc tgc cta aag tcc ccc ggt aga ttc gag aga atc tta     2067
Ile Ala Ser Leu Cys Leu Lys Ser Pro Gly Arg Phe Glu Arg Ile Leu
650                 655                 660                 665 ctc aga gct gca aat acc cac agt tcc gcc aaa cct tgc ggg caa caa     2115
Leu Arg Ala Ala Asn Thr His Ser Ser Ala Lys Pro Cys Gly Gln Gln
                670                 675                 680 tcc att cac ttg gga gga gta ttt gaa ttg caa cca ggt gct tcg gtg     2163
Ser Ile His Leu Gly Gly Val Phe Glu Leu Gln Pro Gly Ala Ser Val
            685                 690                 695 ttt gtc aat gtg act gat cca agc caa gtg agc cat ggc act ggc ttc     2211
Phe Val Asn Val Thr Asp Pro Ser Gln Val Ser His Gly Thr Gly Phe
        700                 705                 710 acg tcc ttt ggc tta ctc aaa ctc gag tgataatcta gata                 2252
Thr Ser Phe Gly Leu Leu Lys Leu Glu
    715                 720

<210> SEQ ID NO 13
<211> LENGTH: 2208
<212> TYPE: DNA
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: CDS
<222> LOCATION: (13)..(2196)
<220> FEATURE:
<221> NAME/KEY: sig_peptide
<222> LOCATION: (13)..(72)
<220> FEATURE:
<221> NAME/KEY: mat_peptide
<222> LOCATION: (73)..(2196)
<220> FEATURE:
<221> NAME/KEY: misc_feature
<222> LOCATION: (73)..(1545)
<223> OTHER INFORMATION: HIV gp120 allele + ProAspPro linker
<220> FEATURE:
<221> NAME/KEY: misc_feature
<222> LOCATION: (1552)..(2196)
<223> OTHER INFORMATION: CD154 extracellular domain long form (amino
      acids 48-261) + Glu binds to CD40

<400> SEQUENCE: 13
aagcttgccg cc atg ctg tat acc tct cag ctg tta gga cta ctt ctg ttt     51
              Met Leu Tyr Thr Ser Gln Leu Leu Gly Leu Leu Leu Phe
              -20                 -15                 -10

| | | |
|---|---|---|
| tgg atc tcg gct tcg aga tcc atg ctc ctt ggg ata ttg atg atc tgt<br>Trp Ile Ser Ala Ser Arg Ser Met Leu Leu Gly Ile Leu Met Ile Cys<br>      -5                -1  1                  5 | | 99 |
| agt gct aca gaa aaa ttg tgg gtc aca gtc tat tat ggg gta cct gtg<br>Ser Ala Thr Glu Lys Leu Trp Val Thr Val Tyr Tyr Gly Val Pro Val<br> 10                 15               20               25 | | 147 |
| tgg aga gaa gca acc acc act cta ttt tgt gca tca gat gct aaa gcc<br>Trp Arg Glu Ala Thr Thr Thr Leu Phe Cys Ala Ser Asp Ala Lys Ala<br>                 30                    35               40 | | 195 |
| tat gat aca gag gta cat aat gtt tgg gcc aca cat gcc tgt gta ccc<br>Tyr Asp Thr Glu Val His Asn Val Trp Ala Thr His Ala Cys Val Pro<br>             45               50               55 | | 243 |
| aca gac ccc aac cca caa gaa gta gta ttg gga aat gtg aca gaa aat<br>Thr Asp Pro Asn Pro Gln Glu Val Val Leu Gly Asn Val Thr Glu Asn<br>         60                 65               70 | | 291 |
| ttt aac atg tgg aaa aat aac atg gta gat cag atg cat gag gat ata<br>Phe Asn Met Trp Lys Asn Asn Met Val Asp Gln Met His Glu Asp Ile<br>     75                 80               85 | | 339 |
| atc agt tta tgg gat gaa agc cta aag cca tgt gta aaa tta acc cca<br>Ile Ser Leu Trp Asp Glu Ser Leu Lys Pro Cys Val Lys Leu Thr Pro<br> 90                 95              100            105 | | 387 |
| ctc tgt gtt act tta aat tgc act aat ttg aat atc act aag aat act<br>Leu Cys Val Thr Leu Asn Cys Thr Asn Leu Asn Ile Thr Lys Asn Thr<br>             110               115             120 | | 435 |
| act aat ccc act agt agc agc tgg gga atg atg gag aaa gga gaa ata<br>Thr Asn Pro Thr Ser Ser Ser Trp Gly Met Met Glu Lys Gly Glu Ile<br>             125               130             135 | | 483 |
| aaa aat tgc tct ttc tat atc acc aca agc ata aga aat aag gta aag<br>Lys Asn Cys Ser Phe Tyr Ile Thr Thr Ser Ile Arg Asn Lys Val Lys<br>         140               145             150 | | 531 |
| aaa gaa tat gca ctt ttt aat aga ctt gat gta gta cca ata gaa aat<br>Lys Glu Tyr Ala Leu Phe Asn Arg Leu Asp Val Val Pro Ile Glu Asn<br>      155              160              165 | | 579 |
| act aat aat act aag tat agg tta ata agt tgt aac acc tca gtc att<br>Thr Asn Asn Thr Lys Tyr Arg Leu Ile Ser Cys Asn Thr Ser Val Ile<br>170                175               180             185 | | 627 |
| aca cag gcc tgt cca aag gta tcc ttt cag cca att ccc ata cat tat<br>Thr Gln Ala Cys Pro Lys Val Ser Phe Gln Pro Ile Pro Ile His Tyr<br>             190               195             200 | | 675 |
| tgt gtc ccg gct ggg ttt gcg atg cta aag tgt aac aat aag aca ttc<br>Cys Val Pro Ala Gly Phe Ala Met Leu Lys Cys Asn Asn Lys Thr Phe<br>         205               210             215 | | 723 |
| aat gga tca gga cca tgc aca aat gtc agc aca gta caa tgt aca cat<br>Asn Gly Ser Gly Pro Cys Thr Asn Val Ser Thr Val Gln Cys Thr His<br>             220               225             230 | | 771 |
| gga att agg cca gtg gtg tca act caa ctg ctg tta aat ggc agt cta<br>Gly Ile Arg Pro Val Val Ser Thr Gln Leu Leu Leu Asn Gly Ser Leu<br>      235              240              245 | | 819 |
| gca gaa gaa gac ata gta att aga tct gaa aat ttc aca gac aat gct<br>Ala Glu Glu Asp Ile Val Ile Arg Ser Glu Asn Phe Thr Asp Asn Ala<br>250                255               260             265 | | 867 |
| aaa acc ata ata gta cag cta aat gaa tct gta gta att aat tgt aca<br>Lys Thr Ile Ile Val Gln Leu Asn Glu Ser Val Val Ile Asn Cys Thr<br>             270               275             280 | | 915 |
| aga ccc aac aac aat aca aga aga agg tta tct ata gga cca ggg aga<br>Arg Pro Asn Asn Asn Thr Arg Arg Arg Leu Ser Ile Gly Pro Gly Arg<br>         285               290             295 | | 963 |
| gca ttt tat gca aga aga aac ata ata gga gat ata aga caa gca cat<br>Ala Phe Tyr Ala Arg Arg Asn Ile Ile Gly Asp Ile Arg Gln Ala His | | 1011 |

```
                   300                 305                 310
tgt aac att agt aga gca aaa tgg aat aac act tta caa cag ata gtt      1059
Cys Asn Ile Ser Arg Ala Lys Trp Asn Asn Thr Leu Gln Gln Ile Val
        315                 320                 325 ata aaa tta aga gaa aaa ttt agg aat aaa aca ata gcc ttt aat caa      1107
Ile Lys Leu Arg Glu Lys Phe Arg Asn Lys Thr Ile Ala Phe Asn Gln
330                 335                 340                 345 tcc tca gga ggg gac cca gaa att gta atg cac agt ttt aat tgt gga      1155
Ser Ser Gly Gly Asp Pro Glu Ile Val Met His Ser Phe Asn Cys Gly
            350                 355                 360 ggg gaa ttc ttc tac tgt aat aca gca caa ctg ttt aat agt act tgg      1203
Gly Glu Phe Phe Tyr Cys Asn Thr Ala Gln Leu Phe Asn Ser Thr Trp
                365                 370                 375 aat gtt act gga ggg aca aat ggc act gaa gga aat gac ata atc aca      1251
Asn Val Thr Gly Gly Thr Asn Gly Thr Glu Gly Asn Asp Ile Ile Thr
                    380                 385                 390 ctc caa tgc aga ata aaa caa att ata aat atg tgg cag aaa gta gga      1299
Leu Gln Cys Arg Ile Lys Gln Ile Ile Asn Met Trp Gln Lys Val Gly
395                 400                 405 aaa gca atg tat gcc cct ccc atc aca gga caa att aga tgt tca tca      1347
Lys Ala Met Tyr Ala Pro Pro Ile Thr Gly Gln Ile Arg Cys Ser Ser
410                 415                 420                 425 aat att aca ggg ctg cta cta aca aga gat gga ggt aat agt act gag      1395
Asn Ile Thr Gly Leu Leu Leu Thr Arg Asp Gly Gly Asn Ser Thr Glu
                430                 435                 440 act gag act gag atc ttc aga cct gga gga gga gat atg agg gac aat      1443
Thr Glu Thr Glu Ile Phe Arg Pro Gly Gly Gly Asp Met Arg Asp Asn
                    445                 450                 455 tgg aga agt gaa tta tat aaa tat aaa gta gta aga att gaa cca ata      1491
Trp Arg Ser Glu Leu Tyr Lys Tyr Lys Val Val Arg Ile Glu Pro Ile
                460                 465                 470 gga gta gca ccc acc agg gca aag aga aga aca gtg caa aga gaa aaa      1539
Gly Val Ala Pro Thr Arg Ala Lys Arg Arg Thr Val Gln Arg Glu Lys
            475                 480                 485 aga ccg gat cca aga agg ttg gac aag ata gaa gat gaa agg aat ctt      1587
Arg Pro Asp Pro Arg Arg Leu Asp Lys Ile Glu Asp Glu Arg Asn Leu
490                 495                 500                 505 cat gaa gat ttt gta ttc atg aaa acg ata cag aga tgc aac aca gga      1635
His Glu Asp Phe Val Phe Met Lys Thr Ile Gln Arg Cys Asn Thr Gly
                510                 515                 520 gaa aga tcc tta tcc tta ctg aac tgt gag gag att aaa agc cag ttt      1683
Glu Arg Ser Leu Ser Leu Leu Asn Cys Glu Glu Ile Lys Ser Gln Phe
                525                 530                 535 gaa ggc ttt gtg aag gat ata atg tta aac aaa gag gag acg aag aaa      1731
Glu Gly Phe Val Lys Asp Ile Met Leu Asn Lys Glu Glu Thr Lys Lys
                540                 545                 550 gaa aac agc ttt gaa atg caa aaa ggt gat cag aat cct caa att gcg      1779
Glu Asn Ser Phe Glu Met Gln Lys Gly Asp Gln Asn Pro Gln Ile Ala
555                 560                 565 gca cat gtc ata agt gag gcc agc agt aaa aca aca tct gtg tta cag      1827
Ala His Val Ile Ser Glu Ala Ser Ser Lys Thr Thr Ser Val Leu Gln
570                 575                 580                 585 tgg gct gaa aaa gga tac tac acc atg agc aac aac ttg gta acc ctg      1875
Trp Ala Glu Lys Gly Tyr Tyr Thr Met Ser Asn Asn Leu Val Thr Leu
                590                 595                 600 gaa aat ggg aaa cag ctg acc gtt aaa aga caa gga ctc tat tat atc      1923
Glu Asn Gly Lys Gln Leu Thr Val Lys Arg Gln Gly Leu Tyr Tyr Ile
                    605                 610                 615 tat gcc caa gtc acc ttc tgt tcc aat cgg gaa gct tcg agt caa gct      1971
```

-continued

```
Tyr Ala Gln Val Thr Phe Cys Ser Asn Arg Glu Ala Ser Ser Gln Ala
        620                 625                 630 cca ttt ata gcc agc ctc tgc cta aag tcc ccc ggt aga ttc gag aga     2019
Pro Phe Ile Ala Ser Leu Cys Leu Lys Ser Pro Gly Arg Phe Glu Arg
        635                 640                 645 atc tta ctc aga gct gca aat acc cac agt tcc gcc aaa cct tgc ggg     2067
Ile Leu Leu Arg Ala Ala Asn Thr His Ser Ser Ala Lys Pro Cys Gly
650                 655                 660                 665 caa caa tcc att cac ttg gga gga gta ttt gaa ttg caa cca ggt gct     2115
Gln Gln Ser Ile His Leu Gly Gly Val Phe Glu Leu Gln Pro Gly Ala
                670                 675                 680 tcg gtg ttt gtc aat gtg act gat cca agc caa gtg agc cat ggc act     2163
Ser Val Phe Val Asn Val Thr Asp Pro Ser Gln Val Ser His Gly Thr
            685                 690                 695 ggc ttc acg tcc ttt ggc tta ctc aaa ctc gag tgataatcta ga           2208
Gly Phe Thr Ser Phe Gly Leu Leu Lys Leu Glu
        700                 705

<210> SEQ ID NO 14
<211> LENGTH: 2070
<212> TYPE: DNA
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: CDS
<222> LOCATION: (13)..(2058)
<220> FEATURE:
<221> NAME/KEY: sig_peptide
<222> LOCATION: (13)..(72)
<220> FEATURE:
<221> NAME/KEY: mat_peptide
<222> LOCATION: (73)..(2058)
<220> FEATURE:
<221> NAME/KEY: misc_feature
<222> LOCATION: (73)..(1587)
<223> OTHER INFORMATION: HIV gp120 allele + (Gly4Ser)3 linker
<220> FEATURE:
<221> NAME/KEY: misc_feature
<222> LOCATION: (1594)..(2058)
<223> OTHER INFORMATION: CD154 extracellular domain from amino acids
      108-261 + Glu binds to CD40

<400> SEQUENCE: 14
aagcttgccg cc atg ctg tat acc tct cag ctg tta gga cta ctt ctg ttt    51
              Met Leu Tyr Thr Ser Gln Leu Leu Gly Leu Leu Leu Phe
                  -20                 -15                 -10 tgg atc tcg gct tcg aga tct atg ctc ctt ggg ata ttg atg atc tgt     99
Trp Ile Ser Ala Ser Arg Ser Met Leu Leu Gly Ile Leu Met Ile Cys
        -5                  -1  1                   5 agt gct aca gaa aaa ttg tgg gtc aca gtc tat tat ggg gta cct gtg    147
Ser Ala Thr Glu Lys Leu Trp Val Thr Val Tyr Tyr Gly Val Pro Val
10                  15                  20                  25 tgg aga gaa gca acc acc act cta ttt tgt gca tca gat gct aaa gcc    195
Trp Arg Glu Ala Thr Thr Thr Leu Phe Cys Ala Ser Asp Ala Lys Ala
                30                  35                  40 tat gat aca gag gta cat aat gtt tgg gcc aca cat gcc tgt gta ccc    243
Tyr Asp Thr Glu Val His Asn Val Trp Ala Thr His Ala Cys Val Pro
            45                  50                  55 aca gac ccc aac cca caa gaa gta gta ttg gga aat gtg aca gaa aat    291
Thr Asp Pro Asn Pro Gln Glu Val Val Leu Gly Asn Val Thr Glu Asn
        60                  65                  70 ttt aac atg tgg aaa aat aac atg gta gat cag atg cat gag gat ata    339
Phe Asn Met Trp Lys Asn Asn Met Val Asp Gln Met His Glu Asp Ile
    75                  80                  85
```

-continued

| | |
|---|---|
| atc agt tta tgg gat gaa agc cta aag cca tgt gta aaa tta acc cca<br>Ile Ser Leu Trp Asp Glu Ser Leu Lys Pro Cys Val Lys Leu Thr Pro<br>90                             95                          100                       105 | 387 |
| ctc tgt gtt act tta aat tgc act aat ttg aat atc act aag aat act<br>Leu Cys Val Thr Leu Asn Cys Thr Asn Leu Asn Ile Thr Lys Asn Thr<br>                       110                         115                       120 | 435 |
| act aat ccc act agt agc agc tgg gga atg atg gag aaa gga gaa ata<br>Thr Asn Pro Thr Ser Ser Ser Trp Gly Met Met Glu Lys Gly Glu Ile<br>                 125                        130                       135 | 483 |
| aaa aat tgc tct ttc tat atc acc aca agc ata aga aat aag gta aag<br>Lys Asn Cys Ser Phe Tyr Ile Thr Thr Ser Ile Arg Asn Lys Val Lys<br>          140                       145                       150 | 531 |
| aaa gaa tat gca ctt ttt aat aga ctt gat gta gta cca ata gaa aat<br>Lys Glu Tyr Ala Leu Phe Asn Arg Leu Asp Val Val Pro Ile Glu Asn<br>155                        160                       165 | 579 |
| act aat aat act aag tat agg tta ata agt tgt aac acc tca gtc att<br>Thr Asn Asn Thr Lys Tyr Arg Leu Ile Ser Cys Asn Thr Ser Val Ile<br>170                        175                       180                   185 | 627 |
| aca cag gcc tgt cca aag gta tcc ttt cag cca att ccc ata cat tat<br>Thr Gln Ala Cys Pro Lys Val Ser Phe Gln Pro Ile Pro Ile His Tyr<br>                       190                         195                       200 | 675 |
| tgt gtc ccg gct ggg ttt gcg atg cta aag tgt aac aat aag aca ttc<br>Cys Val Pro Ala Gly Phe Ala Met Leu Lys Cys Asn Asn Lys Thr Phe<br>                   205                        210                       215 | 723 |
| aat gga tca gga cca tgc aca aat gtc agc aca gta caa tgt aca cat<br>Asn Gly Ser Gly Pro Cys Thr Asn Val Ser Thr Val Gln Cys Thr His<br>          220                       225                       230 | 771 |
| gga att agg cca gtg gtg tca act caa ctg ctg tta aat ggc agt cta<br>Gly Ile Arg Pro Val Val Ser Thr Gln Leu Leu Leu Asn Gly Ser Leu<br>235                        240                       245 | 819 |
| gca gaa gaa gac ata gta att aga tct gaa aat ttc aca gac aat gct<br>Ala Glu Glu Asp Ile Val Ile Arg Ser Glu Asn Phe Thr Asp Asn Ala<br>250                        255                       260                   265 | 867 |
| aaa acc ata ata gta cag cta aat gaa tct gta gta att aat tgt aca<br>Lys Thr Ile Ile Val Gln Leu Asn Glu Ser Val Val Ile Asn Cys Thr<br>                       270                       275                   280 | 915 |
| aga ccc aac aac aat aca aga aga agg tta tct ata gga cca ggg aga<br>Arg Pro Asn Asn Asn Thr Arg Arg Arg Leu Ser Ile Gly Pro Gly Arg<br>          285                       290                       295 | 963 |
| gca ttt tat gca aga aga aac ata ata gga gat ata aga caa gca cat<br>Ala Phe Tyr Ala Arg Arg Asn Ile Ile Gly Asp Ile Arg Gln Ala His<br>          300                       305                       310 | 1011 |
| tgt aac att agt aga gca aaa tgg aat aac act tta caa cag ata gtt<br>Cys Asn Ile Ser Arg Ala Lys Trp Asn Asn Thr Leu Gln Gln Ile Val<br>315                        320                       325 | 1059 |
| ata aaa tta aga gaa aaa ttt agg aat aaa aca ata gcc ttt aat caa<br>Ile Lys Leu Arg Glu Lys Phe Arg Asn Lys Thr Ile Ala Phe Asn Gln<br>330                        335                       340                   345 | 1107 |
| tcc tca gga ggg gac cca gaa att gta atg cac agt ttt aat tgt gga<br>Ser Ser Gly Gly Asp Pro Glu Ile Val Met His Ser Phe Asn Cys Gly<br>                   350                        355                   360 | 1155 |
| ggg gaa ttc ttc tac tgt aat aca gca caa ctg ttt aat agt act tgg<br>Gly Glu Phe Phe Tyr Cys Asn Thr Ala Gln Leu Phe Asn Ser Thr Trp<br>                   365                       370                       375 | 1203 |
| aat gtt act gga ggg aca aat ggc act gaa gga aat gac ata atc aca<br>Asn Val Thr Gly Gly Thr Asn Gly Thr Glu Gly Asn Asp Ile Ile Thr<br>          380                       385                       390 | 1251 |
| ctc caa tgc aga ata aaa caa att ata aat atg tgg cag aaa gta gga<br>Leu Gln Cys Arg Ile Lys Gln Ile Ile Asn Met Trp Gln Lys Val Gly | 1299 |

-continued

| | | | | |
|---|---|---|---|---|
| aaa gca atg tat gcc cct ccc atc aca gga caa att aga tgt tca tca<br>Lys Ala Met Tyr Ala Pro Pro Ile Thr Gly Gln Ile Arg Cys Ser Ser<br>410                   415                  420                  425 | 1347 |

```
                395                 400                 405 aaa gca atg tat gcc cct ccc atc aca gga caa att aga tgt tca tca      1347
Lys Ala Met Tyr Ala Pro Pro Ile Thr Gly Gln Ile Arg Cys Ser Ser
410                 415                 420                 425 aat att aca ggg ctg cta cta aca aga gat gga ggt aat agt act gag      1395
Asn Ile Thr Gly Leu Leu Leu Thr Arg Asp Gly Gly Asn Ser Thr Glu
                430                 435                 440 act gag act gag atc ttc aga cct gga gga gga gat atg agg gac aat      1443
Thr Glu Thr Glu Ile Phe Arg Pro Gly Gly Gly Asp Met Arg Asp Asn
            445                 450                 455 tgg aga agt gaa tta tat aaa tat aaa gta gta aga att gaa cca ata      1491
Trp Arg Ser Glu Leu Tyr Lys Tyr Lys Val Val Arg Ile Glu Pro Ile
        460                 465                 470 gga gta gca ccc acc agg gca aag aga aga aca gtg caa aga gaa aaa      1539
Gly Val Ala Pro Thr Arg Ala Lys Arg Arg Thr Val Gln Arg Glu Lys
    475                 480                 485 aga ggg gga ggc ggt tca gga ggt gga ggt tct gga ggt ggc gga tcg      1587
Arg Gly Gly Gly Gly Ser Gly Gly Gly Gly Ser Gly Gly Gly Gly Ser
490                 495                 500                 505 gat cca gaa aac agc ttt gaa atg caa aaa ggt gat cag aat cct caa      1635
Asp Pro Glu Asn Ser Phe Glu Met Gln Lys Gly Asp Gln Asn Pro Gln
                510                 515                 520 att gcg gca cat gtc ata agt gag gcc agc agt aaa aca aca tct gtg      1683
Ile Ala Ala His Val Ile Ser Glu Ala Ser Ser Lys Thr Thr Ser Val
            525                 530                 535 tta cag tgg gct gaa aaa gga tac tac acc atg agc aac aac ttg gta      1731
Leu Gln Trp Ala Glu Lys Gly Tyr Tyr Thr Met Ser Asn Asn Leu Val
        540                 545                 550 acc ctg gaa aat ggg aaa cag ctg acc gtt aaa aga caa gga ctc tat      1779
Thr Leu Glu Asn Gly Lys Gln Leu Thr Val Lys Arg Gln Gly Leu Tyr
    555                 560                 565 tat atc tat gcc caa gtc acc ttc tgt tcc aat cgg gaa gct tcg agt      1827
Tyr Ile Tyr Ala Gln Val Thr Phe Cys Ser Asn Arg Glu Ala Ser Ser
570                 575                 580                 585 caa gct cca ttt ata gcc agc ctc tgc cta aag tcc ccc ggt aga ttc      1875
Gln Ala Pro Phe Ile Ala Ser Leu Cys Leu Lys Ser Pro Gly Arg Phe
                590                 595                 600 gag aga atc tta ctc aga gct gca aat acc cac agt tcc gcc aaa cct      1923
Glu Arg Ile Leu Leu Arg Ala Ala Asn Thr His Ser Ser Ala Lys Pro
            605                 610                 615 tgc ggg caa caa tcc att cac ttg gga gga gta ttt gaa ttg caa cca      1971
Cys Gly Gln Gln Ser Ile His Leu Gly Gly Val Phe Glu Leu Gln Pro
        620                 625                 630 ggt gct tcg gtg ttt gtc aat gtg act gat cca agc caa gtg agc cat      2019
Gly Ala Ser Val Phe Val Asn Val Thr Asp Pro Ser Gln Val Ser His
    635                 640                 645 ggc act ggc ttc acg tcc ttt ggc tta ctc aaa ctc gag tgataatcta ga   2070
Gly Thr Gly Phe Thr Ser Phe Gly Leu Leu Lys Leu Glu
650                 655                 660

<210> SEQ ID NO 15
<211> LENGTH: 2028
<212> TYPE: DNA
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: CDS
<222> LOCATION: (13)..(2016)
<220> FEATURE:
<221> NAME/KEY: sig_peptide
```

```
<222> LOCATION: (13)..(72)
<220> FEATURE:
<221> NAME/KEY: mat_peptide
<222> LOCATION: (73)..(2016)
<220> FEATURE:
<221> NAME/KEY: misc_feature
<222> LOCATION: (73)..(1551)
<223> OTHER INFORMATION: HIV gp120 allele + ProAspPro linker
<220> FEATURE:
<221> NAME/KEY: misc_feature
<222> LOCATION: (1552)..(2016)
<223> OTHER INFORMATION: CD154 extracellular domain from amino acids
      108-261 + Glu binds to CD40

<400> SEQUENCE: 15
aagcttgccg cc atg ctg tat acc tct cag ctg tta gga cta ctt ctg ttt      51
              Met Leu Tyr Thr Ser Gln Leu Leu Gly Leu Leu Leu Phe
              -20              -15                  -10 tgg atc tcg gct tcg aga tcc atg ctc ctt ggg ata ttg atg atc tgt        99
Trp Ile Ser Ala Ser Arg Ser Met Leu Leu Gly Ile Leu Met Ile Cys
         -5                  -1   1                   5 agt gct aca gaa aaa ttg tgg gtc aca gtc tat tat ggg gta cct gtg       147
Ser Ala Thr Glu Lys Leu Trp Val Thr Val Tyr Tyr Gly Val Pro Val
 10              15                  20                  25 tgg aga gaa gca acc acc act cta ttt tgt gca tca gat gct aaa gcc       195
Trp Arg Glu Ala Thr Thr Thr Leu Phe Cys Ala Ser Asp Ala Lys Ala
             30                  35                  40 tat gat aca gag gta cat aat gtt tgg gcc aca cat gcc tgt gta ccc       243
Tyr Asp Thr Glu Val His Asn Val Trp Ala Thr His Ala Cys Val Pro
             45                  50                  55 aca gac ccc aac cca caa gaa gta gta ttg gga aat gtg aca gaa aat       291
Thr Asp Pro Asn Pro Gln Glu Val Val Leu Gly Asn Val Thr Glu Asn
         60                  65                  70 ttt aac atg tgg aaa aat aac atg gta gat cag atg cat gag gat ata       339
Phe Asn Met Trp Lys Asn Asn Met Val Asp Gln Met His Glu Asp Ile
     75                  80                  85 atc agt tta tgg gat gaa agc cta aag cca tgt gta aaa tta acc cca       387
Ile Ser Leu Trp Asp Glu Ser Leu Lys Pro Cys Val Lys Leu Thr Pro
 90                  95                 100                 105 ctc tgt gtt act tta aat tgc act aat ttg aat atc act aag aat act       435
Leu Cys Val Thr Leu Asn Cys Thr Asn Leu Asn Ile Thr Lys Asn Thr
             110                 115                 120 act aat ccc act agt agc agc tgg gga atg atg gag aaa gga gaa ata       483
Thr Asn Pro Thr Ser Ser Ser Trp Gly Met Met Glu Lys Gly Glu Ile
         125                 130                 135 aaa aat tgc tct ttc tat atc acc aca agc ata aga aat aag gta aag       531
Lys Asn Cys Ser Phe Tyr Ile Thr Thr Ser Ile Arg Asn Lys Val Lys
     140                 145                 150 aaa gaa tat gca ctt ttt aat aga ctt gat gta gta cca ata gaa aat       579
Lys Glu Tyr Ala Leu Phe Asn Arg Leu Asp Val Val Pro Ile Glu Asn
 155                 160                 165 act aat aat act aag tat agg tta ata agt tgt aac acc tca gtc att       627
Thr Asn Asn Thr Lys Tyr Arg Leu Ile Ser Cys Asn Thr Ser Val Ile
170                 175                 180                 185 aca cag gcc tgt cca aag gta tcc ttt cag cca att ccc ata cat tat       675
Thr Gln Ala Cys Pro Lys Val Ser Phe Gln Pro Ile Pro Ile His Tyr
             190                 195                 200 tgt gtc ccg gct ggg ttt gcg atg cta aag tgt aac aat aag aca ttc       723
Cys Val Pro Ala Gly Phe Ala Met Leu Lys Cys Asn Asn Lys Thr Phe
         205                 210                 215 aat gga tca gga cca tgc aca aat gtc agc aca gta caa tgt aca cat       771
Asn Gly Ser Gly Pro Cys Thr Asn Val Ser Thr Val Gln Cys Thr His
     220                 225                 230
```

-continued

| | | |
|---|---|---|
| gga att agg cca gtg gtg tca act caa ctg ctg tta aat ggc agt cta<br>Gly Ile Arg Pro Val Val Ser Thr Gln Leu Leu Leu Asn Gly Ser Leu<br>235              240                        245 | | 819 |
| gca gaa gaa gac ata gta att aga tct gaa aat ttc aca gac aat gct<br>Ala Glu Glu Asp Ile Val Ile Arg Ser Glu Asn Phe Thr Asp Asn Ala<br>250              255                     260              265 | | 867 |
| aaa acc ata ata gta cag cta aat gaa tct gta gta att aat tgt aca<br>Lys Thr Ile Ile Val Gln Leu Asn Glu Ser Val Val Ile Asn Cys Thr<br>                270                     275              280 | | 915 |
| aga ccc aac aac aat aca aga aga agg tta tct ata gga cca ggg aga<br>Arg Pro Asn Asn Asn Thr Arg Arg Arg Leu Ser Ile Gly Pro Gly Arg<br>         285                     290                     295 | | 963 |
| gca ttt tat gca aga aga aac ata ata gga gat ata aga caa gca cat<br>Ala Phe Tyr Ala Arg Arg Asn Ile Ile Gly Asp Ile Arg Gln Ala His<br>300              305                     310 | | 1011 |
| tgt aac att agt aga gca aaa tgg aat aac act tta caa cag ata gtt<br>Cys Asn Ile Ser Arg Ala Lys Trp Asn Asn Thr Leu Gln Gln Ile Val<br>315              320                     325 | | 1059 |
| ata aaa tta aga gaa aaa ttt agg aat aaa aca ata gcc ttt aat caa<br>Ile Lys Leu Arg Glu Lys Phe Arg Asn Lys Thr Ile Ala Phe Asn Gln<br>330              335                     340              345 | | 1107 |
| tcc tca gga ggg gac cca gaa att gta atg cac agt ttt aat tgt gga<br>Ser Ser Gly Gly Asp Pro Glu Ile Val Met His Ser Phe Asn Cys Gly<br>                350                     355              360 | | 1155 |
| ggg gaa ttc ttc tac tgt aat aca gca caa ctg ttt aat agt act tgg<br>Gly Glu Phe Phe Tyr Cys Asn Thr Ala Gln Leu Phe Asn Ser Thr Trp<br>         365                     370                     375 | | 1203 |
| aat gtt act gga ggg aca aat ggc act gaa gga aat gac ata atc aca<br>Asn Val Thr Gly Gly Thr Asn Gly Thr Glu Gly Asn Asp Ile Ile Thr<br>380              385                     390 | | 1251 |
| ctc caa tgc aga ata aaa caa att ata aat atg tgg cag aaa gta gga<br>Leu Gln Cys Arg Ile Lys Gln Ile Ile Asn Met Trp Gln Lys Val Gly<br>395              400                     405 | | 1299 |
| aaa gca atg tat gcc cct ccc atc aca gga caa att aga tgt tca tca<br>Lys Ala Met Tyr Ala Pro Pro Ile Thr Gly Gln Ile Arg Cys Ser Ser<br>410              415                     420              425 | | 1347 |
| aat att aca ggg ctg cta cta aca aga gat gga ggt aat agt act gag<br>Asn Ile Thr Gly Leu Leu Leu Thr Arg Asp Gly Gly Asn Ser Thr Glu<br>                430                     435              440 | | 1395 |
| act gag act gag atc ttc aga cct gga gga gga gat atg agg gac aat<br>Thr Glu Thr Glu Ile Phe Arg Pro Gly Gly Gly Asp Met Arg Asp Asn<br>         445                     450                     455 | | 1443 |
| tgg aga agt gaa tta tat aaa tat aaa gta gta aga att gaa cca ata<br>Trp Arg Ser Glu Leu Tyr Lys Tyr Lys Val Val Arg Ile Glu Pro Ile<br>460              465                     470 | | 1491 |
| gga gta gca ccc acc agg gca aag aga aga aca gtg caa aga gaa aaa<br>Gly Val Ala Pro Thr Arg Ala Lys Arg Arg Thr Val Gln Arg Glu Lys<br>475              480                     485 | | 1539 |
| aga ccg gat cca gaa aac agc ttt gaa atg caa aaa ggt gat cag aat<br>Arg Pro Asp Pro Glu Asn Ser Phe Glu Met Gln Lys Gly Asp Gln Asn<br>490              495                     500              505 | | 1587 |
| cct caa att gcg gca cat gtc ata agt gag gcc agc agt aaa aca aca<br>Pro Gln Ile Ala Ala His Val Ile Ser Glu Ala Ser Ser Lys Thr Thr<br>                510                     515              520 | | 1635 |
| tct gtg tta cag tgg gct gaa aaa gga tac tac acc atg agc aac aac<br>Ser Val Leu Gln Trp Ala Glu Lys Gly Tyr Tyr Thr Met Ser Asn Asn<br>         525                     530                     535 | | 1683 |
| ttg gta acc ctg gaa aat ggg aaa cag ctg acc gtt aaa aga caa gga<br>Leu Val Thr Leu Glu Asn Gly Lys Gln Leu Thr Val Lys Arg Gln Gly | | 1731 |

```
                540             545             550
ctc tat tat atc tat gcc caa gtc acc ttc tgt tcc aat cgg gaa gct    1779
Leu Tyr Tyr Ile Tyr Ala Gln Val Thr Phe Cys Ser Asn Arg Glu Ala
    555                 560                 565 tcg agt caa gct cca ttt ata gcc agc ctc tgc cta aag tcc ccc ggt    1827
Ser Ser Gln Ala Pro Phe Ile Ala Ser Leu Cys Leu Lys Ser Pro Gly
570                 575                 580                 585 aga ttc gag aga atc tta ctc aga gct gca aat acc cac agt tcc gcc    1875
Arg Phe Glu Arg Ile Leu Leu Arg Ala Ala Asn Thr His Ser Ser Ala
                590                 595                 600 aaa cct tgc ggg caa caa tcc att cac ttg gga gga gta ttt gaa ttg    1923
Lys Pro Cys Gly Gln Gln Ser Ile His Leu Gly Gly Val Phe Glu Leu
            605                 610                 615 caa cca ggt gct tcg gtg ttt gtc aat gtg act gat cca agc caa gtg    1971
Gln Pro Gly Ala Ser Val Phe Val Asn Val Thr Asp Pro Ser Gln Val
        620                 625                 630 agc cat ggc act ggc ttc acg tcc ttt ggc tta ctc aaa ctc gag        2016
Ser His Gly Thr Gly Phe Thr Ser Phe Gly Leu Leu Lys Leu Glu
    635                 640                 645 tgataatcta ga                                                       2028

<210> SEQ ID NO 16
<211> LENGTH: 906
<212> TYPE: DNA
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: CDS
<222> LOCATION: (13)..(894)
<220> FEATURE:
<221> NAME/KEY: sig_peptide
<222> LOCATION: (13)..(72)
<220> FEATURE:
<221> NAME/KEY: mat_peptide
<222> LOCATION: (73)..(894)
<220> FEATURE:
<221> NAME/KEY: misc_feature
<222> LOCATION: (73)..(243)
<223> OTHER INFORMATION: HIV gp120 V3 loop + (Gly4Ser)3 linker
<220> FEATURE:
<221> NAME/KEY: misc_feature
<222> LOCATION: (250)..(894)
<223> OTHER INFORMATION: CD154 extracellular domain from amino acids
      48-261 + Glu binds to CD40

<400> SEQUENCE: 16 aagctt

-continued

```
                60                 65                  70
gat ttt gta ttc atg aaa acg ata cag aga tgc aac aca gga gaa aga       339
Asp Phe Val Phe Met Lys Thr Ile Gln Arg Cys Asn Thr Gly Glu Arg
        75                  80                  85 tcc tta tcc tta ctg aac tgt gag gag att aaa agc cag ttt gaa ggc       387
Ser Leu Ser Leu Leu Asn Cys Glu Glu Ile Lys Ser Gln Phe Glu Gly
 90                  95                 100                 105 ttt gtg aag gat ata atg tta aac aaa gag gag acg aag aaa gaa aac       435
Phe Val Lys Asp Ile Met Leu Asn Lys Glu Glu Thr Lys Lys Glu Asn
                110                 115                 120 agc ttt gaa atg caa aaa ggt gat cag aat cct caa att gcg gca cat       483
Ser Phe Glu Met Gln Lys Gly Asp Gln Asn Pro Gln Ile Ala Ala His
            125                 130                 135 gtc ata agt gag gcc agc agt aaa aca aca tct gtg tta cag tgg gct       531
Val Ile Ser Glu Ala Ser Ser Lys Thr Thr Ser Val Leu Gln Trp Ala
        140                 145                 150 gaa aaa gga tac tac acc atg agc aac aac ttg gta acc ctg gaa aat       579
Glu Lys Gly Tyr Tyr Thr Met Ser Asn Asn Leu Val Thr Leu Glu Asn
    155                 160                 165 ggg aaa cag ctg acc gtt aaa aga caa gga ctc tat tat atc tat gcc       627
Gly Lys Gln Leu Thr Val Lys Arg Gln Gly Leu Tyr Tyr Ile Tyr Ala
170                 175                 180                 185 caa gtc acc ttc tgt tcc aat cgg gaa gct tcg agt caa gct cca ttt       675
Gln Val Thr Phe Cys Ser Asn Arg Glu Ala Ser Ser Gln Ala Pro Phe
                190                 195                 200 ata gcc agc ctc tgc cta aag tcc ccc ggt aga ttc gag aga atc tta       723
Ile Ala Ser Leu Cys Leu Lys Ser Pro Gly Arg Phe Glu Arg Ile Leu
            205                 210                 215 ctc aga gct gca aat acc cac agt tcc gcc aaa cct tgc ggg caa caa       771
Leu Arg Ala Ala Asn Thr His Ser Ser Ala Lys Pro Cys Gly Gln Gln
        220                 225                 230 tcc att cac ttg gga gga gta ttt gaa ttg caa cca ggt gct tcg gtg       819
Ser Ile His Leu Gly Gly Val Phe Glu Leu Gln Pro Gly Ala Ser Val
    235                 240                 245 ttt gtc aat gtg act gat cca agc caa gtg agc cat ggc act ggc ttc       867
Phe Val Asn Val Thr Asp Pro Ser Gln Val Ser His Gly Thr Gly Phe
250                 255                 260                 265 acg tcc ttt ggc tta ctc aaa ctc gag tgataatcta ga                     906
Thr Ser Phe Gly Leu Leu Lys Leu Glu
                270
```

<210> SEQ ID NO 17
<211> LENGTH: 864
<212> TYPE: DNA
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: CDS
<222> LOCATION: (13)..(852)
<220> FEATURE:
<221> NAME/KEY: sig_peptide
<222> LOCATION: (13)..(72)
<220> FEATURE:
<221> NAME/KEY: mat_peptide
<222> LOCATION: (73)..(852)
<220> FEATURE:
<221> NAME/KEY: misc_feature
<222> LOCATION: (73)..(207)
<223> OTHER INFORMATION: HIV gp120 allele + (Gly4Ser)3 linker
<220> FEATURE:
<221> NAME/KEY: misc_feature
<222> LOCATION: (208)..(852)
<223> OTHER INFORMATION: CD154 extracellular domain from 48-261 + Glu binds to CD40

<400> SEQUENCE: 17

```
aagcttgccg cc atg ctg tat acc tct cag ctg tta gga cta ctt ctg ttt      51
              Met Leu Tyr Thr Ser Gln Leu Leu Gly Leu Leu Leu Phe
              -20             -15                 -10 tgg atc tcg gct tcg aga tct gta gta att aat tgt aca aga ccc aac        99
Trp Ile Ser Ala Ser Arg Ser Val Val Ile Asn Cys Thr Arg Pro Asn
        -5              -1  1                   5 aac aat aca aga aga agg tta tct ata gga cca ggg aga gca ttt tat       147
Asn Asn Thr Arg Arg Arg Leu Ser Ile Gly Pro Gly Arg Ala Phe Tyr
 10              15                  20                  25 gca aga aga aac ata ata gga gat ata aga caa gca cat tgt aac att       195
Ala Arg Arg Asn Ile Ile Gly Asp Ile Arg Gln Ala His Cys Asn Ile
                 30                  35                  40 agt ccg gat cca aga agg ttg gac aag ata gaa gat gaa agg aat ctt       243
Ser Pro Asp Pro Arg Arg Leu Asp Lys Ile Glu Asp Glu Arg Asn Leu
             45                  50                  55 cat gaa gat ttt gta ttc atg aaa acg ata cag aga tgc aac aca gga       291
His Glu Asp Phe Val Phe Met Lys Thr Ile Gln Arg Cys Asn Thr Gly
         60                  65                  70 gaa aga tcc tta tcc tta ctg aac tgt gag gag att aaa agc cag ttt       339
Glu Arg Ser Leu Ser Leu Leu Asn Cys Glu Glu Ile Lys Ser Gln Phe
     75                  80                  85 gaa ggc ttt gtg aag gat ata atg tta aac aaa gag gag acg aag aaa       387
Glu Gly Phe Val Lys Asp Ile Met Leu Asn Lys Glu Glu Thr Lys Lys
 90              95                 100                 105 gaa aac agc ttt gaa atg caa aaa ggt gat cag aat cct caa att gcg       435
Glu Asn Ser Phe Glu Met Gln Lys Gly Asp Gln Asn Pro Gln Ile Ala
                110                 115                 120 gca cat gtc ata agt gag gcc agc agt aaa aca aca tct gtg tta cag       483
Ala His Val Ile Ser Glu Ala Ser Ser Lys Thr Thr Ser Val Leu Gln
            125                 130                 135 tgg gct gaa aaa gga tac tac acc atg agc aac aac ttg gta acc ctg       531
Trp Ala Glu Lys Gly Tyr Tyr Thr Met Ser Asn Asn Leu Val Thr Leu
        140                 145                 150 gaa aat ggg aaa cag ctg acc gtt aaa aga caa gga ctc tat tat atc       579
Glu Asn Gly Lys Gln Leu Thr Val Lys Arg Gln Gly Leu Tyr Tyr Ile
    155                 160                 165 tat gcc caa gtc acc ttc tgt tcc aat cgg gaa gct tcg agt caa gct       627
Tyr Ala Gln Val Thr Phe Cys Ser Asn Arg Glu Ala Ser Ser Gln Ala
170                 175                 180                 185 cca ttt ata gcc agc ctc tgc cta aag tcc ccc ggt aga ttc gag aga       675
Pro Phe Ile Ala Ser Leu Cys Leu Lys Ser Pro Gly Arg Phe Glu Arg
                190                 195                 200 atc tta ctc aga gct gca aat acc cac agt tcc gcc aaa cct tgc ggg       723
Ile Leu Leu Arg Ala Ala Asn Thr His Ser Ser Ala Lys Pro Cys Gly
            205                 210                 215 caa caa tcc att cac ttg gga gga gta ttt gaa ttg caa cca ggt gct       771
Gln Gln Ser Ile His Leu Gly Gly Val Phe Glu Leu Gln Pro Gly Ala
        220                 225                 230 tcg gtg ttt gtc aat gtg act gat cca agc caa gtg agc cat ggc act       819
Ser Val Phe Val Asn Val Thr Asp Pro Ser Gln Val Ser His Gly Thr
    235                 240                 245 ggc ttc acg tcc ttt ggc tta ctc aaa ctc gag tgataatcta ga             864
Gly Phe Thr Ser Phe Gly Leu Leu Lys Leu Glu
250                 255                 260
```

<210> SEQ ID NO 18
<211> LENGTH: 726

-continued

```
<212> TYPE: DNA
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: CDS
<222> LOCATION: (13)..(714)
<220> FEATURE:
<221> NAME/KEY: sig_peptide
<222> LOCATION: (13)..(72)
<220> FEATURE:
<221> NAME/KEY: mat_peptide
<222> LOCATION: (73)..(714)
<220> FEATURE:
<221> NAME/KEY: misc_feature
<222> LOCATION: (73)..(207)
<223> OTHER INFORMATION: HIV gp120 V3 loop + ProAspPro linker
<220> FEATURE:
<221> NAME/KEY: misc_feature
<222> LOCATION: (208)..(714)
<223> OTHER INFORMATION: CD154 ext

```
Gly Ala Ser Val Phe Val Asn Val Thr Asp Pro Ser Gln Val Ser His
            190                 195                 200 ggc act ggc ttc acg tcc ttt ggc tta ctc aaa ctc gag tgataatcta ga      726
Gly Thr Gly Phe Thr Ser Phe Gly Leu Leu Lys Leu Glu
            205                 210

<210> SEQ ID NO 19
<211> LENGTH: 684
<212> TYPE: DNA
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: CDS
<222> LOCATION: (13)..(672)
<220> FEATURE:
<221> NAME/KEY: sig_peptide
<222> LOCATION: (13)..(72)
<220> FEATURE:
<221> NAME/KEY: mat_peptide
<222> LOCATION: (73)..(672)
<220> FEATURE:
<221> NAME/KEY: misc_feature
<222> LOCATION: (73)..(207)
<223> OTHER INFORMATION: HIV gp120 V3 loop + ProAspPro linker
<220> FEATURE:
<221> NAME/KEY: misc_feature
<222> LOCATION: (208)..(672)
<223> OTHER INFORMATION: CD154 extracellular domain from amino acids
      108-261 + Glu binds to CD40

<400> SEQUENCE: 19
aagcttgccg cc atg

-continued

```
aaa cct tgc ggg caa caa tcc att cac ttg gga gga gta ttt gaa ttg    579
Lys Pro Cys Gly Gln Gln Ser Ile His Leu Gly Gly Val Phe Glu Leu
            155                 160                 165 caa cca ggt gct tcg gtg ttt gtc aat gtg act gat cca agc caa gtg    627
Gln Pro Gly Ala Ser Val Phe Val Asn Val Thr Asp Pro Ser Gln Val
170                 175                 180                 185 agc cat ggc act ggc ttc acg tcc ttt ggc tta ctc aaa ctc gag        672
Ser His Gly Thr Gly Phe Thr Ser Phe Gly Leu Leu Lys Leu Glu
                190                 195                 200 tgataatcta ga                                                       684
```

<210> SEQ ID NO 20
<211> LENGTH: 742
<212> TYPE: PRT
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: SIGNAL
<222> LOCATION: (1)..(20)
<223> OTHER INFORMATION: Synthetic secretory signal peptide
<220> FEATURE:
<221> NAME/KEY: DOMAIN
<222> LOCATION: (21)..(526)
<223> OTHER INFORMATION: HIV gp120 domain with (Gly4Ser)3 linker
<220> FEATURE:
<221> NAME/KEY: BINDING
<222> LOCATION: (529)..(742)
<223> OTHER INFORMATION: CD154 extracellular domain long -continued

```
                190                 195                 200
Ala Gly Phe Ala Met Leu Lys Cys Asn Asn Lys Thr Phe Asn Gly Ser
205                 210                 215                 220

Gly Pro Cys Thr Asn Val Ser Thr Val Gln Cys Thr His Gly Ile Arg
                225                 230                 235

Pro Val Val Ser Thr Gln Leu Leu Asn Gly Ser Leu Ala Glu Glu
                240                 245                 250

Asp Ile Val Ile Arg Ser Glu Asn Phe Thr Asp Asn Ala Lys Thr Ile
                255                 260                 265

Ile Val Gln Leu Asn Glu Ser Val Val Ile Asn Cys Thr Arg Pro Asn
            270                 275                 280

Asn Asn Thr Arg Arg Arg Leu Ser Ile Gly Pro Gly Arg Ala Phe Tyr
285                 290                 295                 300

Ala Arg Arg Asn Ile Ile Gly Asp Ile Arg Gln Ala His Cys Asn Ile
                305                 310                 315

Ser Arg Ala Lys Trp Asn Asn Thr Leu Gln Gln Ile Val Ile Lys Leu
                320                 325                 330

Arg Glu Lys Phe Arg Asn Lys Thr Ile Ala Phe Asn Gln Ser Ser Gly
                335                 340                 345

Gly Asp Pro Glu Ile Val Met His Ser Phe Asn Cys Gly Gly Glu Phe
                350                 355                 360

Phe Tyr Cys Asn Thr Ala Gln Leu Phe Asn Ser Thr Trp Asn Val Thr
365                 370                 375                 380

Gly Gly Thr Asn Gly Thr Glu Gly Asn Asp Ile Ile Thr Leu Gln Cys
                385                 390                 395

Arg Ile Lys Gln Ile Ile Asn Met Trp Gln Lys Val Gly Lys Ala Met
                400                 405                 410

Tyr Ala Pro Pro Ile Thr Gly Gln Ile Arg Cys Ser Ser Asn Ile Thr
                415                 420                 425

Gly Leu Leu Leu Thr Arg Asp Gly Gly Asn Ser Thr Glu Thr Glu Thr
                430                 435                 440

Glu Ile Phe Arg Pro Gly Gly Gly Asp Met Arg Asp Asn Trp Arg Ser
445                 450                 455                 460

Glu Leu Tyr Lys Tyr Lys Val Val Arg Ile Glu Pro Ile Gly Val Ala
                465                 470                 475

Pro Thr Arg Ala Lys Arg Arg Thr Val Gln Arg Glu Lys Arg Gly Gly
                480                 485                 490

Gly Gly Ser Gly Gly Gly Ser Gly Gly Gly Ser Asp Pro Arg
                495                 500                 505

Arg Leu Asp Lys Ile Glu Asp Glu Arg Asn Leu His Glu Asp Phe Val
                510                 515                 520

Phe Met Lys Thr Ile Gln Arg Cys Asn Thr Gly Glu Arg Ser Leu Ser
525                 530                 535                 540

Leu Leu Asn Cys Glu Glu Ile Lys Ser Gln Phe Glu Gly Phe Val Lys
                545                 550                 555

Asp Ile Met Leu Asn Lys Glu Glu Thr Lys Lys Glu Asn Ser Phe Glu
                560                 565                 570

Met Gln Lys Gly Asp Gln Asn Pro Gln Ile Ala Ala His Val Ile Ser
                575                 580                 585

Glu Ala Ser Ser Lys Thr Thr Ser Val Leu Gln Trp Ala Glu Lys Gly
                590                 595                 600

Tyr Tyr Thr Met Ser Asn Asn Leu Val Thr Leu Glu Asn Gly Lys Gln
605                 610                 615                 620
```

-continued

```
Leu Thr Val Lys Arg Gln Gly Leu Tyr Tyr Ile Tyr Ala Gln Val Thr
                625                 630                 635

Phe Cys Ser Asn Arg Glu Ala Ser Ser Gln Ala Pro Phe Ile Ala Ser
                640                 645                 650

Leu Cys Leu Lys Ser Pro Gly Arg Phe Glu Arg Ile Leu Leu Arg Ala
                655                 660                 665

Ala Asn Thr His Ser Ser Ala Lys Pro Cys Gly Gln Gln Ser Ile His
                670                 675                 680

Leu Gly Gly Val Phe Glu Leu Gln Pro Gly Ala Ser Val Phe Val Asn
685                 690                 695                 700

Val Thr Asp Pro Ser Gln Val Ser His Gly Thr Gly Phe Thr Ser Phe
                705                 710                 715

Gly Leu Leu Lys Leu Glu
                720

<210> SEQ ID NO 21
<211> LENGTH: 728
<212> TYPE: PRT
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: SIGNAL
<222> LOCATION: (1)..(20)
<223> OTHER INFORMATION: Synthetic secretory signal peptide
<220> FEATURE:
<221> NAME/KEY: DOMAIN
<222> LOCATION: (21)..(513)
<223> OTHER INFORMATION: HIV gp120 domain with ProAspPro linker
<220> FEATURE:
<221> NAME/KEY: BINDING
<222> LOCATION: (514)..(728)
<223> OTHER INFORMATION: CD154 extracellular domain long -continued

```
Ala Leu Phe Asn Arg Leu Asp Val Val Pro Ile Glu Asn Thr Asn Asn
                160                 165                 170
Thr Lys Tyr Arg Leu Ile Ser Cys Asn Thr Ser Val Ile Thr Gln Ala
            175                 180                 185
Cys Pro Lys Val Ser Phe Gln Pro Ile Pro Ile His Tyr Cys Val Pro
        190                 195                 200
Ala Gly Phe Ala Met Leu Lys Cys Asn Asn Lys Thr Phe Asn Gly Ser
205                 210                 215                 220
Gly Pro Cys Thr Asn Val Ser Thr Val Gln Cys Thr His Gly Ile Arg
                225                 230                 235
Pro Val Val Ser Thr Gln Leu Leu Asn Gly Ser Leu Ala Glu Glu
            240                 245                 250
Asp Ile Val Ile Arg Ser Glu Asn Phe Thr Asp Asn Ala Lys Thr Ile
        255                 260                 265
Ile Val Gln Leu Asn Glu Ser Val Val Ile Asn Cys Thr Arg Pro Asn
    270                 275                 280
Asn Asn Thr Arg Arg Arg Leu Ser Ile Gly Pro Gly Arg Ala Phe Tyr
285                 290                 295                 300
Ala Arg Arg Asn Ile Ile Gly Asp Ile Arg Gln Ala His Cys Asn Ile
                305                 310                 315
Ser Arg Ala Lys Trp Asn Asn Thr Leu Gln Gln Ile Val Ile Lys Leu
            320                 325                 330
Arg Glu Lys Phe Arg Asn Lys Thr Ile Ala Phe Asn Gln Ser Ser Gly
        335                 340                 345
Gly Asp Pro Glu Ile Val Met His Ser Phe Asn Cys Gly Gly Glu Phe
    350                 355                 360
Phe Tyr Cys Asn Thr Ala Gln Leu Phe Asn Ser Thr Trp Asn Val Thr
365                 370                 375                 380
Gly Gly Thr Asn Gly Thr Glu Gly Asn Asp Ile Ile Thr Leu Gln Cys
                385                 390                 395
Arg Ile Lys Gln Ile Ile Asn Met Trp Gln Lys Val Gly Lys Ala Met
            400                 405                 410
Tyr Ala Pro Pro Ile Thr Gly Gln Ile Arg Cys Ser Ser Asn Ile Thr
        415                 420                 425
Gly Leu Leu Leu Thr Arg Asp Gly Gly Asn Ser Thr Glu Thr Glu Thr
    430                 435                 440
Glu Ile Phe Arg Pro Gly Gly Gly Asp Met Arg Asp Asn Trp Arg Ser
445                 450                 455                 460
Glu Leu Tyr Lys Tyr Lys Val Val Arg Ile Glu Pro Ile Gly Val Ala
                465                 470                 475
Pro Thr Arg Ala Lys Arg Arg Thr Val Gln Arg Glu Lys Arg Pro Asp
            480                 485                 490
Pro Arg Arg Leu Asp Lys Ile Glu Asp Glu Arg Asn Leu His Glu Asp
        495                 500                 505
Phe Val Phe Met Lys Thr Ile Gln Arg Cys Asn Thr Gly Glu Arg Ser
    510                 515                 520
Leu Ser Leu Leu Asn Cys Glu Glu Ile Lys Ser Gln Phe Glu Gly Phe
525                 530                 535                 540
Val Lys Asp Ile Met Leu Asn Lys Glu Thr Lys Lys Glu Asn Ser
                545                 550                 555
Phe Glu Met Gln Lys Gly Asp Gln Asn Pro Gln Ile Ala Ala His Val
            560                 565                 570
Ile Ser Glu Ala Ser Ser Lys Thr Thr Ser Val Leu Gln Trp Ala Glu
```

-continued

```
        575                 580                 585

Lys Gly Tyr Tyr Thr Met Ser Asn Asn Leu Val Thr Leu Glu Asn Gly
    590                 595                 600

Lys Gln Leu Thr Val Lys Arg Gln Gly Leu Tyr Tyr Ile Tyr Ala Gln
605                 610                 615                 620

Val Thr Phe Cys Ser Asn Arg Glu Ala Ser Ser Gln Ala Pro Phe Ile
                625                 630                 635

Ala Ser Leu Cys Leu Lys Ser Pro Gly Arg Phe Glu Arg Ile Leu Leu
            640                 645                 650

Arg Ala Ala Asn Thr His Ser Ser Ala Lys Pro Cys Gly Gln Gln Ser
        655                 660                 665

Ile His Leu Gly Gly Val Phe Glu Leu Gln Pro Gly Ala Ser Val Phe
    670                 675                 680

Val Asn Val Thr Asp Pro Ser Gln Val Ser His Gly Thr Gly Phe Thr
685                 690                 695                 700

Ser Phe Gly Leu Leu Lys Leu Glu
                705

<210> SEQ ID NO 22
<211> LENGTH: 682
<212> TYPE: PRT
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: SIGNAL
<222> LOCATION: (1)..(20)
<223> OTHER INFORMATION: Synthetic secretory signal peptide
<220> FEATURE:
<221> NAME/KEY: DOMAIN
<222> LOCATION: (21)..(525)
<223> OTHER INFORMATION: HIV gp120 domain with (Gly4Ser)3 linker
<220> FEATURE:
<221> NAME/KEY: BINDING
<222> LOCATION: (528)..(682)
<223> OTHER INFORMATION: CD154 extracellular domain long form amino
      acids 108(Glu) to 261(Leu) + Glu binds CD40

<400> SEQUENCE: 22

Met Leu Tyr Thr Ser Gln Leu Leu Gly Leu Leu Leu Phe Trp Ile Ser
-20                 -15                 -10                  -5

Ala Ser Arg Ser Met Leu Leu Gly Ile Leu Met Ile Cys Ser Ala Thr
             -1   1               5                  10

Glu Lys Leu Trp Val Thr Val Tyr Tyr Gly Val Pro Val Trp Arg Glu
         15                  20                  25

Ala Thr Thr Thr Leu Phe Cys Ala Ser Asp Ala Lys Ala Tyr Asp Thr
     30                  35                  40

Glu Val His Asn Val Trp Ala Thr His Ala Cys Val Pro Thr Asp Pro
 45                  50                  55                  60

Asn Pro Gln Glu Val Val Leu Gly Asn Val Thr Glu Asn Phe Asn Met
                 65                  70                  75

Trp Lys Asn Asn Met Val Asp Gln Met His Glu Asp Ile Ile Ser Leu
             80                  85                  90

Trp Asp Glu Ser Leu Lys Pro Cys Val Lys Leu Thr Pro Leu Cys Val
         95                 100                 105

Thr Leu Asn Cys Thr Asn Leu Asn Ile Thr Lys Asn Thr Thr Asn Pro
    110                 115                 120

Thr Ser Ser Ser Trp Gly Met Met Glu Lys Gly Glu Ile Lys Asn Cys
125                 130                 135                 140
```

-continued

```
Ser Phe Tyr Ile Thr Thr Ser Ile Arg Asn Lys Val Lys Lys Glu Tyr
            145                 150                 155
Ala Leu Phe Asn Arg Leu Asp Val Val Pro Ile Glu Asn Thr Asn Asn
        160                 165                 170
Thr Lys Tyr Arg Leu Ile Ser Cys Asn Thr Ser Val Ile Thr Gln Ala
    175                 180                 185
Cys Pro Lys Val Ser Phe Gln Pro Ile Pro Ile His Tyr Cys Val Pro
190                 195                 200
Ala Gly Phe Ala Met Leu Lys Cys Asn Asn Lys Thr Phe Asn Gly Ser
205                 210                 215                 220
Gly Pro Cys Thr Asn Val Ser Thr Val Gln Cys Thr His Gly Ile Arg
            225                 230                 235
Pro Val Val Ser Thr Gln Leu Leu Asn Gly Ser Leu Ala Glu Glu
        240                 245                 250
Asp Ile Val Ile Arg Ser Glu Asn Phe Thr Asp Asn Ala Lys Thr Ile
    255                 260                 265
Ile Val Gln Leu Asn Glu Ser Val Val Ile Asn Cys Thr Arg Pro Asn
270                 275                 280
Asn Asn Thr Arg Arg Arg Leu Ser Ile Gly Pro Gly Arg Ala Phe Tyr
285                 290                 295                 300
Ala Arg Arg Asn Ile Ile Gly Asp Ile Arg Gln Ala His Cys Asn Ile
            305                 310                 315
Ser Arg Ala Lys Trp Asn Asn Thr Leu Gln Gln Ile Val Ile Lys Leu
        320                 325                 330
Arg Glu Lys Phe Arg Asn Lys Thr Ile Ala Phe Asn Gln Ser Ser Gly
    335                 340                 345
Gly Asp Pro Glu Ile Val Met His Ser Phe Asn Cys Gly Gly Glu Phe
350                 355                 360
Phe Tyr Cys Asn Thr Ala Gln Leu Phe Asn Ser Thr Trp Asn Val Thr
365                 370                 375                 380
Gly Gly Thr Asn Gly Thr Glu Gly Asn Asp Ile Ile Thr Leu Gln Cys
            385                 390                 395
Arg Ile Lys Gln Ile Ile Asn Met Trp Gln Lys Val Gly Lys Ala Met
        400                 405                 410
Tyr Ala Pro Pro Ile Thr Gly Gln Ile Arg Cys Ser Ser Asn Ile Thr
    415                 420                 425
Gly Leu Leu Leu Thr Arg Asp Gly Gly Asn Ser Thr Glu Thr Glu Thr
430                 435                 440
Glu Ile Phe Arg Pro Gly Gly Gly Asp Met Arg Asp Asn Trp Arg Ser
445                 450                 455                 460
Glu Leu Tyr Lys Tyr Lys Val Val Arg Ile Glu Pro Ile Gly Val Ala
            465                 470                 475
Pro Thr Arg Ala Lys Arg Arg Thr Val Gln Arg Glu Lys Arg Gly Gly
        480                 485                 490
Gly Gly Ser Gly Gly Gly Gly Ser Gly Gly Gly Gly Ser Asp Pro Glu
    495                 500                 505
Asn Ser Phe Glu Met Gln Lys Gly Asp Gln Asn Pro Gln Ile Ala Ala
510                 515                 520
His Val Ile Ser Glu Ala Ser Ser Lys Thr Thr Ser Val Leu Gln Trp
525                 530                 535                 540
Ala Glu Lys Gly Tyr Tyr Thr Met Ser Asn Asn Leu Val Thr Leu Glu
            545                 550                 555
```

```
Asn Gly Lys Gln Leu Thr Val Lys Arg Gln Gly Leu Tyr Tyr Ile Tyr
            560                 565                 570

Ala Gln Val Thr Phe Cys Ser Asn Arg Glu Ala Ser Ser Gln Ala Pro
        575                 580                 585

Phe Ile Ala Ser Leu Cys Leu Lys Ser Pro Gly Arg Phe Glu Arg Ile
    590                 595                 600

Leu Leu Arg Ala Ala Asn Thr His Ser Ala Lys Pro Cys Gly Gln
605                 610                 615                 620

Gln Ser Ile His Leu Gly Gly Val Phe Glu Leu Gln Pro Gly Ala Ser
                625                 630                 635

Val Phe Val Asn Val Thr Asp Pro Ser Gln Val Ser His Gly Thr Gly
                640                 645                 650

Phe Thr Ser Phe Gly Leu Leu Lys Leu Glu
            655                 660
```

<210> SEQ ID NO 23
<211> LENGTH: 668
<212> TYPE: PRT
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: SIGNAL
<222> LOCATION: (1)..(20)
<223> OTHER INFORMATION: Synthetic secretory signal peptide
<220> FEATURE:
<221> NAME/KEY: DOMAIN
<222> LOCATION: (21)..(513)
<223> OTHER INFORMATION: HIV gp120 domain with ProAspPro linker
<220> FEATURE:
<221> NAME/KEY: BINDING
<222> LOCATION: (514)..(668)
<223> OTHER INFORMATION: CD154 extracellular domain long form amino
      acids -continued

```
            160                 165                 170
Thr Lys Tyr Arg Leu Ile Ser Cys Asn Thr Ser Val Ile Thr Gln Ala
            175                 180                 185
Cys Pro Lys Val Ser Phe Gln Pro Ile Pro Ile His Tyr Cys Val Pro
            190                 195                 200
Ala Gly Phe Ala Met Leu Lys Cys Asn Asn Lys Thr Phe Asn Gly Ser
205                 210                 215                 220
Gly Pro Cys Thr Asn Val Ser Thr Val Gln Cys Thr His Gly Ile Arg
                225                 230                 235
Pro Val Val Ser Thr Gln Leu Leu Asn Gly Ser Leu Ala Glu Glu
            240                 245                 250
Asp Ile Val Ile Arg Ser Glu Asn Phe Thr Asp Asn Ala Lys Thr Ile
            255                 260                 265
Ile Val Gln Leu Asn Glu Ser Val Ile Asn Cys Thr Arg Pro Asn
            270                 275                 280
Asn Asn Thr Arg Arg Leu Ser Ile Gly Pro Gly Arg Ala Phe Tyr
285                 290                 295                 300
Ala Arg Arg Asn Ile Ile Gly Asp Ile Arg Gln Ala His Cys Asn Ile
                305                 310                 315
Ser Arg Ala Lys Trp Asn Asn Thr Leu Gln Gln Ile Val Ile Lys Leu
            320                 325                 330
Arg Glu Lys Phe Arg Asn Lys Thr Ile Ala Phe Asn Gln Ser Ser Gly
            335                 340                 345
Gly Asp Pro Glu Ile Val Met His Ser Phe Asn Cys Gly Gly Glu Phe
            350                 355                 360
Phe Tyr Cys Asn Thr Ala Gln Leu Phe Asn Ser Thr Trp Asn Val Thr
365                 370                 375                 380
Gly Gly Thr Asn Gly Thr Glu Gly Asn Asp Ile Ile Thr Leu Gln Cys
                385                 390                 395
Arg Ile Lys Gln Ile Ile Asn Met Trp Gln Lys Val Gly Lys Ala Met
                400                 405                 410
Tyr Ala Pro Pro Ile Thr Gly Gln Ile Arg Cys Ser Ser Asn Ile Thr
            415                 420                 425
Gly Leu Leu Leu Thr Arg Asp Gly Gly Asn Ser Thr Glu Thr Glu Thr
430                 435                 440
Glu Ile Phe Arg Pro Gly Gly Gly Asp Met Arg Asp Asn Trp Arg Ser
445                 450                 455                 460
Glu Leu Tyr Lys Tyr Lys Val Val Arg Ile Glu Pro Ile Gly Val Ala
                465                 470                 475
Pro Thr Arg Ala Lys Arg Arg Thr Val Gln Arg Glu Lys Arg Pro Asp
            480                 485                 490
Pro Glu Asn Ser Phe Glu Met Gln Lys Gly Asp Gln Asn Pro Gln Ile
            495                 500                 505
Ala Ala His Val Ile Ser Glu Ala Ser Ser Lys Thr Thr Ser Val Leu
            510                 515                 520
Gln Trp Ala Glu Lys Gly Tyr Tyr Thr Met Ser Asn Asn Leu Val Thr
525                 530                 535                 540
Leu Glu Asn Gly Lys Gln Leu Thr Val Lys Arg Gln Gly Leu Tyr Tyr
                545                 550                 555
Ile Tyr Ala Gln Val Thr Phe Cys Ser Asn Arg Glu Ala Ser Ser Gln
                560                 565                 570
Ala Pro Phe Ile Ala Ser Leu Cys Leu Lys Ser Pro Gly Arg Phe Glu
575                 580                 585
```

-continued

```
Arg Ile Leu Leu Arg Ala Ala Asn Thr His Ser Ser Ala Lys Pro Cys
    590                 595                 600

Gly Gln Gln Ser Ile His Leu Gly Gly Val Phe Glu Leu Gln Pro Gly
605                 610                 615                 620

Ala Ser Val Phe Val Asn Val Thr Asp Pro Ser Gln Val Ser His Gly
                625                 630                 635

Thr Gly Phe Thr Ser Phe Gly Leu Leu Lys Leu Glu
            640                 645

<210> SEQ ID NO 24
<211> LENGTH: 294
<212> TYPE: PRT
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: SIGNAL
<222> LOCATION: (1)..(20)
<223> OTHER INFORMATION: Synthetic secretory signal peptide
<220> FEATURE:
<221> NAME/KEY: DOMAIN
<222> LOCATION: (21)..(77)
<223> OTHER INFORMATION: HIV gp120 V3 loop with (Gly4Ser)3 linker
<220> FEATURE:
<221> NAME/KEY: BINDING
<222> LOCATION: (80)..(294)
<223> OTHER INFORMATION: CD154 extracellular domain long form am

```
Leu Cys Leu Lys Ser Pro Gly Arg Phe Glu Arg Ile Leu Leu Arg Ala
205                 210                 215                 220

Ala Asn Thr His Ser Ser Ala Lys Pro Cys Gly Gln Gln Ser Ile His
                225                 230                 235

Leu Gly Gly Val Phe Glu Leu Gln Pro Gly Ala Ser Val Phe Val Asn
                240                 245                 250

Val Thr Asp Pro Ser Gln Val Ser His Gly Thr Gly Phe Thr Ser Phe
                255                 260                 265

Gly Leu Leu Lys Leu Glu
        270

<210> SEQ ID NO 25
<211> LENGTH: 280
<212> TYPE: PRT
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: SIGNAL
<222> LOCATION: (1)..(20)
<223> OTHER INFORMATION: Synthetic secretory signal peptide
<220> FEATURE:
<221> NAME/KEY: DOMAIN
<222> LOCATION: (21)..(65)
<223> OTHER INFORMATION: HIV gp120 V3 loop with ProAspPro linker
<220> F -continued

```
                    190                 195                 200
Arg Ala Ala Asn Thr His Ser Ser Ala Lys Pro Cys Gly Gln Gln Ser
205                 210                 215                 220

Ile His Leu Gly Gly Val Phe Glu Leu Gln Pro Gly Ala Ser Val Phe
                225                 230                 235

Val Asn Val Thr Asp Pro Ser Gln Val Ser His Gly Thr Gly Phe Thr
                240                 245                 250

Ser Phe Gly Leu Leu Lys Leu Glu
            255                 260

<210> SEQ ID NO 26
<211> LENGTH: 234
<212> TYPE: PRT
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: SIGNAL
<222> LOCATION: (1)..(20)
<223> OTHER INFORMATION: Synthetic secretory signal peptide
<220> FEATURE:
<221> NAME/KEY: DOMAIN
<222> LOCATION: (21)..(77)
<223> OTHER INFORMATION: HIV gp120 V3 loop with (Gly4Ser)3 linker
<220> FEATURE:
<221> NAME/KEY: BINDING
<222> LOCATION: (80)..(234)
<223> OTHER INFORMATION: CD154 ext

```
Phe Thr Ser Phe Gly Leu Leu Lys Leu Glu
205                 210
```

<210> SEQ ID NO 27
<211> LENGTH: 220
<212> TYPE: PRT
<213> ORGANISM: Artificial Sequence
<220> FEATURE:
<223> OTHER INFORMATION: Description of Artificial Sequence: Synthetic
      HIV-human fusion construct
<220> FEATURE:
<221> NAME/KEY: SIGNAL
<222> LOCATION: (1)..(20)
<223> OTHER INFORMATION: Synthetic secretory signal peptide
<220> FEATURE:
<221> NAME/KEY: DOMAIN
<222> LOCATION: (21)..(65)
<223> OTHER INFORMATION: HIV gp120 V3 loop with ProAspPro linker
<220> FEATURE:
<221> NAME/KEY: BINDING
<222> LOCATION: (66)..(220)
<223> OTHER INFORMATION: CD154 extracellular domain long form amino
      acids 108(Glu) to 261(Leu) + Glu binds CD40

<400> SEQUENCE: 27

```
Met Leu Tyr Thr Ser Gln Leu Leu Gly Leu Leu Leu Phe Trp Ile Ser
-20             -15                 -10                  -5

Ala Ser Arg Ser Val Val Ile Asn Cys Thr Arg Pro Asn Asn Asn

-continued

```
  1               5

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Linker
      peptide

<400> SEQUENCE: 29

Gly Gly Gly Gly Ser Gly Gly Gly Gly Ser Gly Gly Gly Gly Ser
  1               5                  10                  15
```